(12) United States Patent
Poisner

(10) Patent No.: US 12,733,825 B2
(45) Date of Patent: Sep. 15, 2026

(54) SOLID STATE SENSOR

(71) Applicant: Certus Critical Care, Inc., Salt Lake City, UT (US)

(72) Inventor: David Poisner, Carmichael, CA (US)

(73) Assignee: Certus Critical Care, Inc., Salt Lake City, UT (US)

( * ) Notice: Subject to any disclaimer, the term of this patent is extended or adjusted under 35 U.S.C. 154(b) by 649 days.

(21) Appl. No.: 18/324,938

(22) Filed: May 26, 2023

(65) Prior Publication Data

US 2023/0380702 A1 Nov. 30, 2023

Related U.S. Application Data

(60) Provisional application No. 63/346,286, filed on May 26, 2022.

(51) Int. Cl.
*A61B 5/021* (2006.01)

(52) U.S. Cl.
CPC ................................ *A61B 5/02108* (2013.01)

(58) Field of Classification Search
USPC .......................................................... 324/612
See application file for complete search history.

(56) References Cited

U.S. PATENT DOCUMENTS 6,911,872 B2 6/2005 Shah et al.
8,387,464 B2 3/2013 McNeil et al.
(Continued)

FOREIGN PATENT DOCUMENTS

CN 108627286 A 10/2018
CN 108700482 A 10/2018
(Continued)

OTHER PUBLICATIONS

Danneels H., et al., "A fully-digital, 0.3V, 270 nW capacitive sensor interface without external references", ESSCIRC (ESSCIRC), 2011 Proceedings of the, IEEE, Sep. 12, 2011 (Sep. 12, 2011), pp. 287-290.
(Continued)

*Primary Examiner* — Farhana A Hoque
(74) *Attorney, Agent, or Firm* — COOLEY LLP

(57) ABSTRACT

Described herein are solid state sensors for measuring various physical parameters. The solid state sensors may be used in systems, devices, and methods for controlling blood flow or for measuring (e.g., monitoring) blood pressure. In some instances, the method may include obtaining a first count number indicating a number of oscillations at a first ring oscillator circuit during a sample period. The first ring oscillator circuit may be associated with a sensor and oscillates at a first oscillation rate. The first oscillation rate may be based on a first set of physical parameters and a second physical parameter. The method may further include obtaining a second count number indicating a number of oscillations at a second ring oscillator circuit during the sample period. The second ring oscillator circuit may be associated with the sensor and oscillates at a second oscillation rate. The second oscillation rate may be based on the first of physical parameters but not the second physical parameter. The method may further include determining a value associated with the second physical parameter at the sensor based on the first count number and the second count number.

42 Claims, 27 Drawing Sheets

(56) References Cited

U.S. PATENT DOCUMENTS

| | | | |
|---|---|---|---|
| 11,464,703 | B2 | 10/2022 | Johnson et al. |
| 11,596,411 | B2 | 3/2023 | Johnson et al. |
| 11,602,592 | B2 | 3/2023 | Johnson et al. |
| 11,633,192 | B2 | 4/2023 | Johnson et al. |
| 11,839,585 | B2 | 12/2023 | Johnson et al. |
| 12,251,111 | B2 | 3/2025 | Johnson |
| 2005/0118977 | A1* | 6/2005 | Drogi ........................ H04B 1/40 455/323 |
| 2013/0001550 | A1 | 1/2013 | Seeger et al. |
| 2013/0208763 | A1* | 8/2013 | Uwe .................. G06K 19/0717 374/171 |
| 2018/0147375 | A1 | 5/2018 | Johnson et al. |
| 2019/0064026 | A1 | 2/2019 | Kollmitzer et al. |
| 2021/0275783 | A1* | 9/2021 | Johnson ............... A61B 5/7275 |
| 2021/0322026 | A1 | 10/2021 | Johnson et al. |
| 2022/0239312 | A1* | 7/2022 | Akondy Raja Raghupathi ........... H03M 3/438 |
| 2022/0401709 | A1 | 12/2022 | Beeby et al. |
| 2023/0079117 | A1 | 3/2023 | Beeby et al. |
| 2023/0138661 | A1 | 5/2023 | Mohlin et al. |
| 2023/0270444 | A1 | 8/2023 | Fong |
| 2023/0338037 | A1 | 10/2023 | Johnson et al. |
| 2023/0355866 | A1 | 11/2023 | Johnson et al. |
| 2023/0414220 | A1 | 12/2023 | Johnson et al. |
| 2024/0082104 | A1 | 3/2024 | Johnson et al. |
| 2024/0165380 | A1 | 5/2024 | Williams et al. |
| 2025/0221629 | A1 | 7/2025 | Poisner et al. |

FOREIGN PATENT DOCUMENTS

| | | | |
|---|---|---|---|
| EP | 1907811 | B1 | 4/2012 |
| EP | 2775264 | A2 | 9/2014 |
| EP | 3321654 | B1 | 1/2020 |
| EP | 3772640 | A1 | 2/2021 |
| WO | WO-2016196837 | A1 | 12/2016 |
| WO | WO-2018089837 | A1 | 5/2018 |
| WO | WO-2018132623 | A1 | 7/2018 |
| WO | WO-2018195507 | A1 | 10/2018 |
| WO | WO-2021178937 | A1 | 9/2021 |
| WO | WO-2021188602 | A2 | 9/2021 |
| WO | WO-2022266397 | A2 | 12/2022 |
| WO | WO-2023043513 | A1 | 3/2023 |
| WO | WO-2023086344 | A1 | 5/2023 |
| WO | WO-2023224679 | A2 | 11/2023 |
| WO | WO-2023230630 | A1 | 11/2023 |
| WO | WO-2024228736 | A2 | 11/2024 |
| WO | WO-2025117909 | A1 | 6/2025 |

OTHER PUBLICATIONS

Invitation to Pay Additional Fees mailed on Sep. 19, 2023, for PCT Application No. PCT/US2023/067585, filed on May 26, 2023, 14 pages.

Nagata T., et al., "Digital compensated capacitive pressure sensor using CMOS technology for low pressure measurements", Transducers. San Francisco, Jun. 24-27, 1991; [Proceedings of the International Conference on Solid State Sensors and Actuators], New York, IEEE, US, Jun. 24, 1991 (Jun. 24, 1991), pp. 308-311.

PCT Application No. PCT/US2023/067585, International Search Report and Written Opinion mailed Nov. 10, 2023; Applicant Certus Critical Care, Inc.; 18 pages.

PCT Application No. PCT/US2024/057983, International Search Report and Written Opinion mailed May 13, 2025; Applicant Certus Critical Care, Inc.; 19 pages.

PCT Application No. PCT/US2024/057983, Invitation to Pay Additional Fees mailed Mar. 21, 2025; Applicant Certus Critical Care, Inc.; 10 pages.

* cited by examiner

200

700

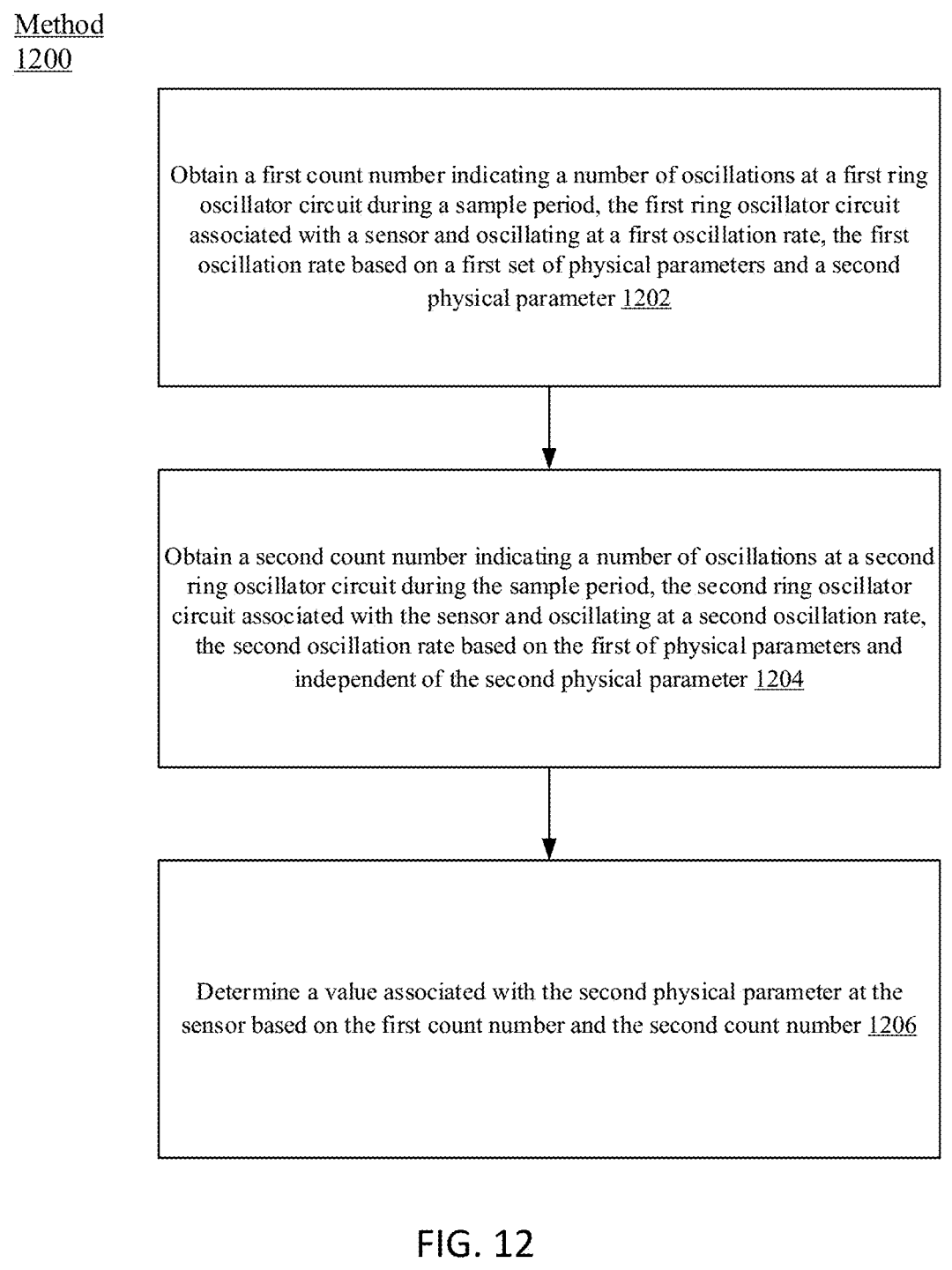

Method 1200

Obtain a first count number indicating a number of oscillations at a first ring oscillator circuit during a sample period, the first ring oscillator circuit associated with a sensor and oscillating at a first oscillation rate, the first oscillation rate based on a first set of physical parameters and a second physical parameter 1202

Obtain a second count number indicating a number of oscillations at a second ring oscillator circuit during the sample period, the second ring oscillator circuit associated with the sensor and oscillating at a second oscillation rate, the second oscillation rate based on the first of physical parameters and independent of the second physical parameter 1204

Determine a value associated with the second physical parameter at the sensor based on the first count number and the second count number 1206

FIG. 12

Frame N
Byte1 Byte2 Byte3 Byte4 Byte5
Frame N+1
Byte1 Byte2 Byte3 ...

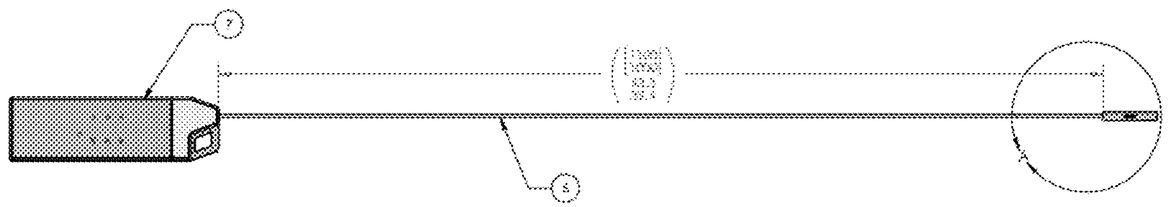
FIG. 22A
10
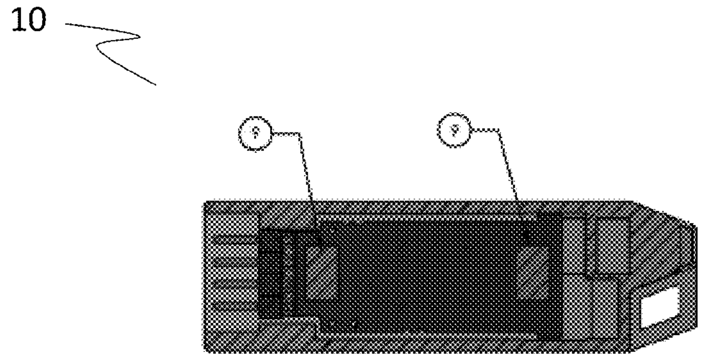
FIG. 22B
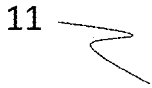
11
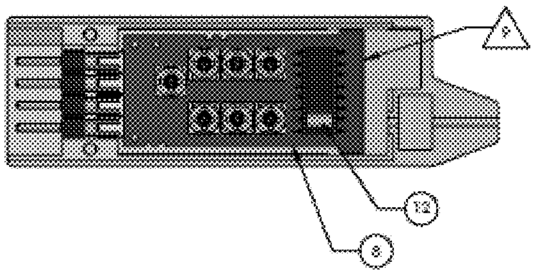
FIG. 22C

SOLID STATE SENSOR

CROSS-REFERENCE TO RELATED APPLICATIONS

This application claims priority to U.S. Provisional Application No. 63/346,286, filed on May 26, 2022, which is hereby incorporated by reference in its entirety.

TECHNICAL FIELD

Devices, systems, and methods herein relate to a sensor that may be used to measure a parameter, including but not limited to pressure.

BACKGROUND

Sensors may be configured to measure various physical properties. For example, Wheatstone bridge sensors may include a piezoresistive circuit on a silicon-based die and may be configured as a pressure sensor or a strain gauge. However, piezoresistive sensor measurements are subject to an inherent resistor offset and inherent temperature offset that may be mitigated by an offset compensation circuit that may comprise one or more of a differential amplifier, potentiometer, Digital-to-Analog Converter (DAC), Analog-to-Digital Converter (ADC), resistors, and the like. Furthermore, the wires coupling the sensor to an electronic circuit may have a length (e.g., 500 mm or more) that functions as an antenna that picks up common mode noise. A differential low-pass filter and a differential amplifier may be used to provide high common-mode rejection for the wires. The circuits needed to compensate for sensor offsets and wire noise increases the cost, size, weight, and manufacturing complexity of a sensor. Accordingly, additional devices, systems, and methods of measuring a parameter may be desirable.

SUMMARY

Described here are systems, devices, and methods including a sensor useful for measuring one or more parameters (e.g., physical properties) including, but not limited to, pressure (e.g., blood pressure). In some variations, the sensor may be part of a device that controls blood flow, for example, as one or more of a sensor proximal to an expandable member (e.g., balloon), a sensor distal to an expandable member, and a sensor within an expandable member. In other variations, the sensor may be included in a device that measures pressure (e.g., blood pressure) without controlling blood flow. One or more sensors may be used to measure the one or more parameters. For example, a plurality of sensors (e.g., two, three, four or more) may be used to measure the same parameter, each of a plurality of sensors may be used to measure different parameters, or a plurality of sensors may be employed where some of the plurality of sensors may be used to measure the same parameter and some of the plurality of sensors may be used to measure different parameters. Each sensor may be contained within its own sensor housing, or a plurality of sensors may be contained within a single sensor housing. In some variations, the sensor housing containing one or more sensors may be integrated into an elongate body (e.g., catheter) as described in more detail herein. In one variation, the sensor may comprise a first circuit configured to receive an input clock signal and output a first output clock signal having a predetermined ratio between the input clock signal and the first output clock signal using an adjustable delay, a second circuit configured to receive the input clock signal and output a second output clock signal using the adjustable delay, and a third circuit coupled to the first circuit and the second circuit, the third circuit configured to generate a third signal based on a difference between the first output clock signal and the second output clock signal.

In some variations, the first output clock signal may vary based on a first set of parameters and the second output clock signal may vary based on a second set of parameters different from the first set of parameters. In some of these variations, the first set of parameters may comprise one or more of temperature and voltage. In some of these variations, the second set of parameters may comprise temperature, voltage, and one or more of force, pressure, light amplitude, audio amplitude, and resistance or capacitance corresponding to a chemical or physical reaction.

In some variations, the third signal may correspond to one or more of temperature, voltage, force, pressure, light amplitude, and audio amplitude. In some variations, a frequency of the first output clock signal and the second output clock signal may be each greater than a frequency of the input clock signal. In some variations, the first circuit may comprise a first plurality of delay circuits arranged in a ring configuration. In some of these variations, the first plurality of delay circuits may comprise a first plurality of inverter circuits and a first adjustable delay circuit. In some of these variations, the first adjustable delay circuit may comprise a rate counter. In some of these variations, the first plurality of inverter circuits may be coupled to a first multiplexer. In some of these variations, the first plurality of inverter circuits may be configured in a closed loop with positive feedback.

In some variations, the first delay circuit may comprise a first resistor-capacitor delay circuit. In some variations, the second circuit may comprise one or more of a resistor-capacitor delay circuit, a resistor-inductor delay circuit, and a capacitive delay circuit. In some variations, the first circuit may comprise a first oscillator circuit.

In some variations, a fourth circuit may be coupled to the third circuit, the fourth configured to receive the input clock signal and output a fourth output clock signal using the adjustable delay. The third circuit may be configured to generate a fifth signal based on a difference between the first output clock signal and the fourth output clock signal. In some of these variations, the fifth signal may correspond to one or more of temperature, voltage, force, pressure, light amplitude, and audio amplitude.

In some variations, a substrate may comprise the first circuit, the second circuit, and the third circuit. In some variations, a first substrate may comprise one of the first circuit and the second circuit, and a second substrate may comprise the other of the first circuit and the second circuit.

In some variations, a fourth circuit may be configured to output the third signal as a digital signal. In some variations, a fourth circuit may be configured to output the third signal as a set of binary encoded bits at a periodic rate. In some variations, the fourth circuit may comprise one or more of a wire and an antenna.

Also described here are methods of measuring a parameter comprising receiving an input clock signal, generating a first output clock signal having a predetermined ratio between the input clock signal and the first output clock signal using an adjustable delay, generating a second output clock signal using the adjustable delay, and generating a third signal based on a difference between the first output clock signal and the second output clock signal.

In some variations, the first output clock signal may vary based on a first set of parameters and the second output clock signal may vary based on a second set of parameters different from the first set of parameters. In some variations, the first set of parameters may comprise one or more of temperature and voltage. In some variations, the second set of parameters may comprise temperature, voltage, and one or more of force, pressure, light amplitude, audio amplitude, and resistance or capacitance corresponding to a chemical or physical reaction.

In some variations, the third signal may correspond to one or more of temperature, voltage, force, pressure, light amplitude, and audio amplitude. In some variations, a frequency of the first output clock signal and the second output clock signal may be each greater than a frequency of the input clock signal.

In some variations, a fourth output clock signal may be generated using the adjustable delay, and a fifth signal may be generated based on a difference between the first output clock signal and the fourth output clock signal. In some variations, the fifth signal corresponds to one or more of temperature, voltage, force, pressure, light amplitude, and audio amplitude.

In some variations, the third signal may be output as a digital signal. In some variations, the third signal may be output as a set of binary encoded bits at a periodic rate.

Also described herein is a sensor including a first ring oscillator circuit oscillating at a first oscillation rate. The first oscillation rate may be based on a first set of physical parameters and a second physical parameter. The sensor may further include a second ring oscillator circuit oscillating at a second oscillation rate. The second oscillation rate may be based on the first of physical parameters but not the second physical parameter. The sensor may further include a first rate counter circuit operatively coupled to the first ring oscillator circuit and configured to count a first number of oscillations at the first ring oscillator circuit during a sample period. The sensor may further include a second rate counter circuit operatively coupled to the second ring oscillator circuit and configured to count a second number of oscillations at the second ring oscillator circuit during the sample period. The sensor may further include circuitry configured to receive representations of the first number of oscillations and the second number of oscillations, and generate a value associated with the second physical parameter at the sensor based on the first number of oscillations and the second number of oscillations in response to receiving the representations of the first number of oscillations and the second number of oscillations.

Also described herein is a sensor. The sensor includes a first ring oscillator circuit oscillating at a first oscillation rate. The first oscillation rate may be based on a first set of physical parameters and a second physical parameter. The sensor may further include a second ring oscillator circuit oscillating at a second oscillation rate. The second oscillation rate may be based on the first of physical parameters but not the second physical parameter. The sensor may further include a first rate counter circuit operatively coupled to the first ring oscillator circuit and configured to count a first number of oscillations at the first ring oscillator circuit during a sample period. The sensor may further include a second rate counter circuit operatively coupled to the second ring oscillator circuit and configured to count a second number of oscillations at the second ring oscillator circuit during the sample period. The sensor may further include communication circuitry configured to send representations of the first number of oscillations and the second number of oscillations to processing circuitry operatively coupled to the communication circuitry to cause the processing circuitry to generate a value associated the second physical parameter at the sensor based on the first number of oscillations and the second number of oscillations in response to receiving the representations of the first number of oscillations and the second number of oscillations form the communication circuitry.

Also described herein is a method that includes obtaining a first count number indicating a number of oscillations at a first ring oscillator circuit during a sample period. The first ring oscillator circuit may be associated with a sensor and oscillate at a first oscillation rate. The first oscillation rate may be based on a first set of physical parameters and a second physical parameter. The method may further include obtaining a second count number indicating a number of oscillations at a second ring oscillator circuit during the sample period. The second ring oscillator circuit may be associated with the sensor and oscillate at a second oscillation rate. The second oscillation rate may be based on the first of physical parameters and independent of the second physical parameter. The method may further include determining a value associated with the second physical parameter at the sensor based on the first count number and the second count number.

Also described herein is a method that may include measuring a first value for a first parameter using a first sensor, sending the first value to a second sensor coupled to the first sensor, and measuring a second value for a second parameter using the second sensor. The method may further include producing a serial value that includes the first value and the second value.

Devices configured to monitor a physiologic condition or adjust a physiologic parameter (e.g., blood flow or blood pressure) of a patient are also described herein. These devices may include any one or more of the sensors described herein integrated into an elongate body (e.g., a catheter). In some variations, the one or more sensors may be configured to measure blood pressure. When the sensor(s) are included in a blood flow control device, a balloon may be coupled to the elongate body and configured for placement within a blood vessel. The one or more sensors may be contained within a sensor housing, which may protect the sensor(s) from damage due to body fluids (e.g., blood) or pressurization from the balloon of a blood flow control device. The sensor housing may be formed from any suitable material, e.g, a polymer, metal, or a metal alloy. In some variations, the sensor housing is made from stainless steel. In other variations, the sensor(s) may be entirely or partially encapsulated in the polymer within the sensor housing.

Additionally, devices configured to monitor blood pressure are also described herein. The devices may include any one or more of the sensors described herein that measure blood pressure integrated into an elongate body (e.g., a catheter). The one or more sensors may be contained within a sensor housing, as described above, to help protect the sensor(s) from damage due to body fluids (e.g., blood) or other external factors. In some variations, the sensor and/or the sensor housing may be tubular in shape, and have a diameter of about 1 Fr. The sensor(s) may be entirely or partially encapsulated in the polymer within the sensor housing. When the sensor is coupled to a PCBA (printed circuit board assembly) housing, the housing may include an adhesive configured to attach the PCBA housing to the skin of a patient. The adhesive in some instances may be provided as an adhesive patch.

BRIEF DESCRIPTION OF THE DRAWINGS

FIG. 12 depicts a flowchart of an exemplary method of determining a value associated with a physical parameter of interest at a sensor.

FIGS. 22A-22C show an exemplary pressure sensing device incorporating a sensor as described herein.

DETAILED DESCRIPTION

Figure 1A:
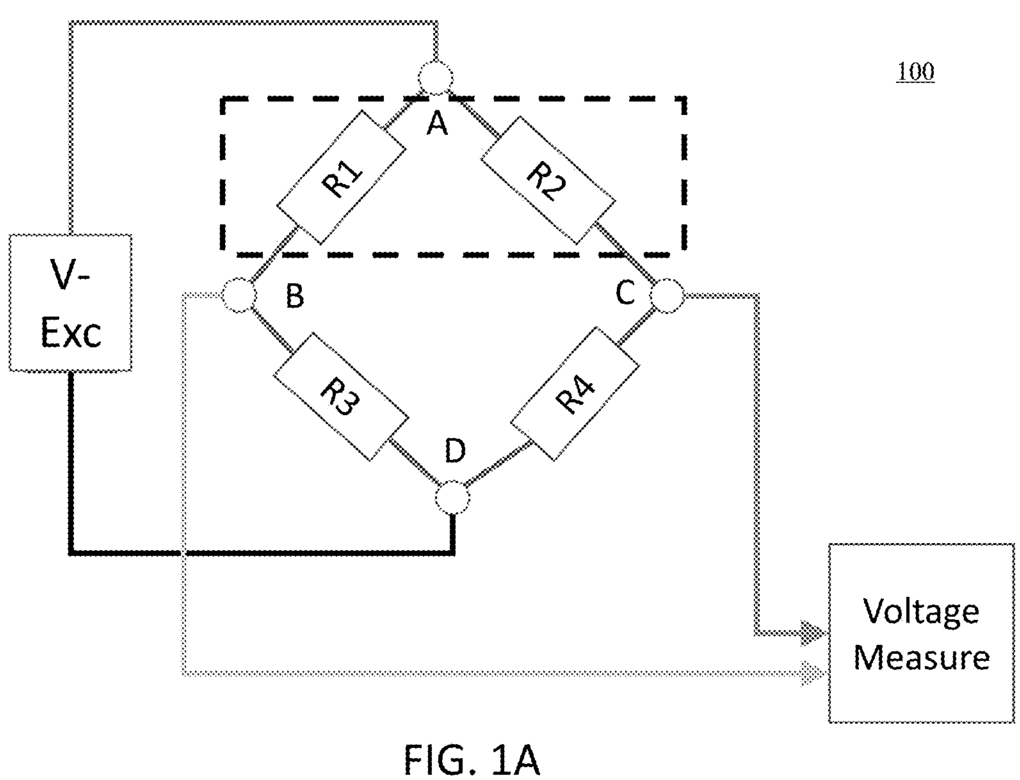
FIGS. 1A and 1B are schematic diagrams of conventional Wheatstone bridge sensors.

Described here are systems, devices, and methods for measuring a parameter (e.g., a physical property) including but not limited to temperature, voltage, force, pressure, light amplitude, and audio amplitude. For example, in some implementations, the systems, devices, and methods described herein may comprise a sensor configured to measure a change in electrical propagation time (e.g., delay) corresponding to a physical property. The sensor may be coupled to a compute device (e.g., microcontroller) configured to receive output from the sensor, determine the measured value of the parameter, and optionally output (e.g., display) the measured value and/or send an indication of the measured value to another compute device. The sensors may be disposed within a sensor housing to help protect the sensor from fluids (e.g., blood) and/or damage due to other external elements. The sensors may be contained in, positioned within, and/or encapsulated in a sensor housing and integrated into an elongate body (e.g., a catheter) used in various devices, for example, blood flow control devices and pressure monitoring devices, as further described herein.

The systems, devices, and methods described herein may inherently compensate for variations in temperature, voltage, silicon skew, common mode noise, and the like, and may be useful for medical, automotive, aviation, and industrial applications, especially with size and/or weight constraints. By contrast, conventional PLL multipliers require complex analog modeling of a silicon process and commonly have issues at specific combinations of temperature, voltage, and/or speed of the silicon. However, conventional compensation solutions such as additional circuit elements including a differential amplifier, a differential low-pass filter, offset compensation, and an analog-to-digital converters (ADC) are not needed for the systems, devices, and methods described herein.

Sensors

Generally, the sensors described herein may comprise a plurality of compensated ring clock multipliers (e.g., oscillator ring circuits) configured to generate and output an accurate higher speed clock signal from a lower speed clock signal. An adjustable delay may be calculated for the output clock signal of a first oscillator ring circuit corresponding to a first set of parameters (e.g., temperature, voltage, silicon die). A second oscillator ring circuit may be configured to generate and output a second clock signal that varies in response to the first set of parameters and at least one additional parameter (e.g., pressure). The difference between the output clock signals corresponds to a measurement of the sensed parameter (e.g., pressure) that inherently compensates for the first set of parameters (e.g., temperature, voltage, silicon die). Additional oscillator ring circuits may be used to measure additional parameters. Moreover, in some variations, the measured parameter may be output as a digital signal which may increase immunity to electrostatic discharge.

FIGS. 1A, 1B, 2A and 2B illustrate conventional sensors and their various limitations and drawbacks relative to the inventions described herein. FIG. 1A is a schematic diagram of a conventional Wheatstone bridge sensor 100 (e.g., pressure sensor, strain gauge) including resistors R1, R2, R3, and R4 coupled to a voltage source V and a voltage measurement circuit. As shown in FIG. 1A, R1 and R2 form the sensor element (e.g., half Wheatstone bridge) and the resistors R3 and R4 have a fixed resistance. For example, a change in pressure corresponds to a change in R1 and/or R2. For example, an increase in pressure may correspond to an increase in R1 and a decrease in R2. In particular, pressure is proportional to a differential voltage across the bridge voltage $V_{BC}$. If R1 equals R2 and R3 equals R4, then the voltage $V_{BC}$ will be 0 V, and the current through R1 and R3 will be the same as the current through R2 and R4. However, if R1 and/or R2 change (e.g., due to a change in pressure), then the voltage $V_{BC}$ will increase or decrease accordingly and may be measured by the voltage measurement circuit. The change in pressure may then be measured based on $V_{BC}$.

In some variations, conventional Wheatstone bridge sensors separate R3 and R4 from the sensor elements R1 and R2. Furthermore, R3 and R4 may be set to be as close in resistance as possible. For example, R1 does not need to equal R3 so long as R3 is equal to R4 such that $V_{BC}$ will depend on the ratio of R1 and R2. However, $V_{BC}$ may comprise an error (e.g., offset) when R3 does not equal R4. This offset may be measured and used to calibrate the sensor (e.g., when the sensor is manufactured or turned on). For example, the sensor may be calibrated by measuring $V_{BC}$ at first and second predetermined pressures. The inherent offset and gain of the sensor circuit may be determined using linear regression such that the sensor may be calibrated.

Similarly, R1 and R2 do not need to have any inherent relationship at any one condition. For example, R1 may be 2000.5 ohms and R2 may be 2002.1 ohms at ambient pressure, and $V_{BC}$ may not be 0 V when R3 equals R4. However, the inherent offset may be removed in the pressure measurement so long as another measurement is made at a different pressure.

Figure 1B:
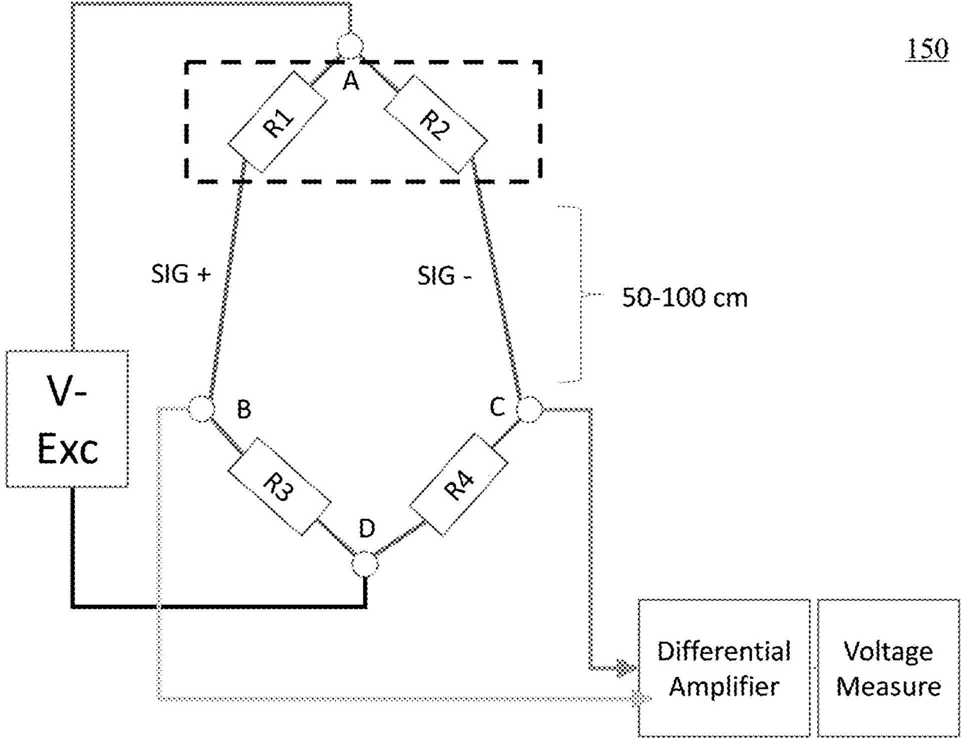

FIG. 1B is a schematic diagram of another Wheatstone bridge sensor 150 where the sensor elements R1 and R2 are farther away from the rest of the circuit. For example, when used in a blood flow control device, such as an endovascular balloon catheter, R1 and R2 may be inside the body and about 50 cm to about 100 cm away from the rest of the circuit (e.g., V, R3, and R4). For example, a Wheatstone bridge circuit configured as a pressure sensor preferably has a dimension smaller than a diameter of a body lumen (e.g., artery, vein) in which it is placed. In some variations, the pressure sensor may comprise R1 and/or R2 and a set of wires (e.g., three wires—a wire from V to R1 and R2, a wire from R1 to R3, and a wire from R2 to R4) to connect to the remaining elements of the circuit disposed external to the patient. Furthermore, the voltages and/or currents applied to the pressure sensor may be relatively low to reduce heat and patient risk if the sensor and/or wires are damaged. For example, resistances R1-R4 may be about 2K ohms and the voltage applied to the pressure sensor may be between about 2 V and about 5 V such that the current is below about 1 mA. For these values, the differential voltage $V_{BC}$ may vary between about 10 μV per mmHg and about 20 μV per mmHg of pressure change. A voltage measurement circuit having a resolution of less than about 5 μV may be configured to provide a pressure measurement resolution of about 0.25 mmHg. However, an amplifier configured to amplify at about 200 times or more is typically needed.

However, when used in this configuration in, for example, a blood flow control device, the length of the wires may reduce sensor accuracy. For example, the wires may function as antennas that pick up both common mode noise and differential noise. Conventionally, removal of this common mode noise requires a common-mode low pass filter, and even with the filter may still require a differential amplifier with a high common mode rejection ratio. Furthermore, the wires are generally not matched such that a differential low-pass filter is typically used to filter the differential signal before input to a differential amplifier. Even so, the low-pass filter itself may add very low frequency offsets, phase delays in the signal, and attenuation at higher heartbeat rates that must be compensated in software.

Conventional sensors are subject to different offsets that may reduce measurement accuracy. In some variations, a conventional sensor may comprise an offset compensation circuit comprising one or more of a differential amplifier, potentiometer, and a DAC configured to compensate for the inherent offset introduced by R1 and R2. However, even the offset compensation circuit may add a small gain error to the measurements. Furthermore, silicon-based sensor may be sensitive to temperature changes. For example, a 1° C. change in temperature may correspond to a greater than 1 mmHg change in offset. In some variations, an offset compensation circuit may comprise one or more of a circuit configured to individually measure the individual voltages $V_B$ and $V_C$, a resistor, and an ADC configured to measure the current of the entire Wheatstone bridge. The design and implementation of the offset compensation circuit may result in extra cost, size, weight, and manufacturing complexity.

Figure 2A:
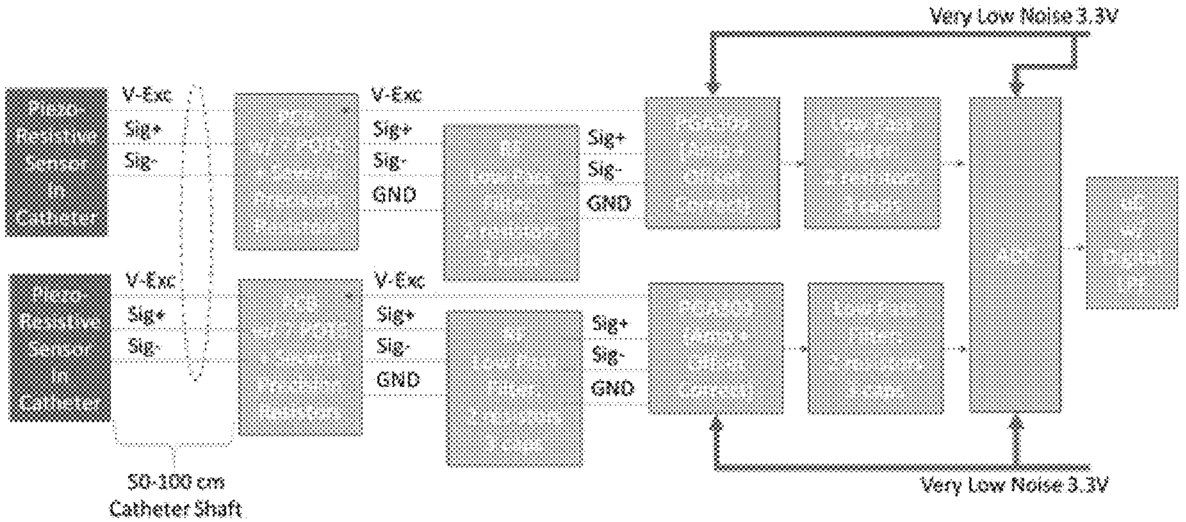
FIGS. 2A and 2B are schematic block diagrams of conventional sensors.

FIG. 2A is a schematic block diagram of a sensor used within a medical device that includes some electronics inside the body and some electronics outside the body. The piezo-resistive MEMS sensor may be conceptualized as incorporated R1 and R3 (from FIGS. 1B and 1C), with R2 and R4 being implemented in a circuit that is mounted on a small Printed Circuit board (PCB).

While solid state pressure transduction (SSPT) circuitry like that shown in FIG. 2A is known, there are some limitations. For example, one limitation relates to balancing the bridge. In addition to R2 and R4, the small PCB also includes several potentiometers (variable resistors) that must be adjusted in order to get the default value of VOut to be in a range such that it is within the capabilities of the amplifier and the Analog to Digital Converter (ADC). For example, if the value for VOut at 0 mmHg pressure is too high, then at a higher pressure (such as 200 mmHg), the output of the amplifier may be greater than the ADC can measure. If the system is to measure negative pressures and the amplifier and ADC are simplified to avoid measuring negative voltages, the value for VOut would be greater than 0 at the lowest pressure. At manufacturing, the potentiometers could be adjusted such that VOut is relatively small at 0 mmHg. Even with these potentiometer adjustments, additional offset adjustments using active circuits, such as in a chip like the PGA309, may be used to compensate for variations due to different barometric pressures, handling negative pressures, and other variations that happen at other stages in the manufacturing process. These characteristics may impact the manufacturing and testing costs for SSPTs.

Another limitation is due to power supply and ground noise. The Wheatstone bridge arrangement is susceptible to electrical noise on the V-Exc signal that feeds current into R1 and R3 (as shown in FIGS. 1B and 1C). Any noise on that line may result in a corresponding variation on VOut. Similarly, if the electrical ground shifts, the stray capacitances and asymmetries in the resistances may result in significant variations in VOut. Further along the path, the amplifier and the ADC may not have identical responses to the shifts in the supply voltages or ground, and so these voltage variations may show up as noise in the measured values.

Another limitation is due to electrical noise on the long wires in the catheter. A wire may act as an unintended antenna, and the 50 to 100 cm wires in the catheter may have an undesired amount gain for a wide range of frequencies. The energy captured by wires (aka antenna effect) changes the intended values, and this change is called "noise". The noise may be dynamic, and may have frequencies from a few Hertz (Hz) to hundreds of millions of Hertz. This type of noise is generally known as Radio Frequency (RF) Noise. Specifically the 60 Hz alternating current (AC) power currently used in the USA and the 50 Hz AC currently used in Europe may result in particularly high noise levels.

As shown in FIG. 1B, the excitation voltage (V-Exc) is directly coupled to resistors R1 and R2 of the Wheatstone bridge. If electrical noise (e.g., variation) is picked up on the V-EXC wire, then this will have the same effect as power supply noise. If the noise is picked up on just the SIG+ or SIG− wires, this will also directly vary VOut. If the same noise is picked up simultaneously on both the SIG+ and SIG− wires, then this creates "common mode" noise. An ideal differential amplifier will ignore this noise, since it in theory doesn't change the difference between the voltages on SIG+ and SIG−. However, in practice, the various resistances and capacitance along the two paths are not identical, and this common mode noise into the amplifier results in a difference.

As a result of the noise limitations, a set of filters are often used. A first differential filter is often used before VOut is presented to the amplifier. This filters out high frequency common mode noise as well as some of the differential noise. Then another low pass filter is placed after the amplifier. This cuts high frequency noise that would cause the ADC to "alias" the noise to lower frequencies. Finally, a digital low-pass filter is sometimes used in the software to remove any noise that is captured by the ADC.

Some of the electrical noise can be difficult to filter, such as that found in common emergency scenarios—electrosurgery pen usage and cardiac defibrillation. Regulatory agencies have acknowledged this limitation and specifications such as 60601-1 and 60601-2-34 allow for a recovery time after the large noise ceases.

Another limitation of SSPT relates to runtime calibration. At the time SSPT is used, there may be variations in the voltage supplied to the sensors, to the amplifier, and to the ADC chip. These variations may be due to changes in the temperature of those circuits. They may also be due to changes in the output of the various power supplies, especially those that are powered by batteries. The sensors may also have variation with respect to temperature. This often requires additional circuitry and manufacturing costs to compensate for the variations due to temperature.

Another limitation of SSPT relates to interoperability. For a REBOA catheter with SSPT sensors above and below the balloon and a display unit outside the body, it can sometimes be desirable to have the catheter itself can be interchangeable so that only one display unit is needed to service multiple catheters. Because the calibration must be performed on the entire analog circuit (sensors in the catheter plus the electronics in the display unit), the interchangeable "boundary" would need to be at the ADC. This may require a separate chassis for the analog circuits and the digital circuits and would add even more cost.

Figure 2B:
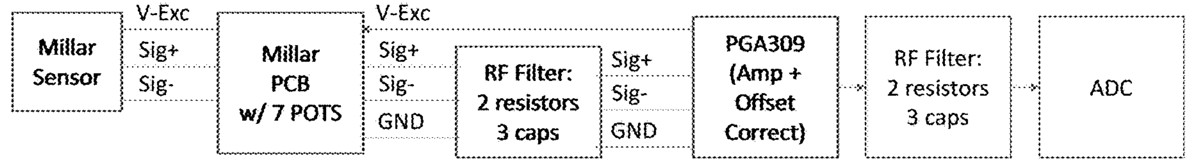

FIG. 2B is a schematic block diagram of a conventional analog path for a sensor 200 such as a Millar sensor which may have a relatively small differential voltage variation per mmHg. For example, the sensor 200 may have a μV/V/mmHg variation where a 2.74V excitation of the Wheatstone bridge may correspond to a 13.7 μV/mmHg. An amplification of more than 200 times may be required for achieving sufficient resolution to allow use of 3.3V ADC. An offset compensation circuit may include the PGA309 chip configured to compensate for an offset and adjust the gain so that the output is within a predetermined range of the ADC. The systems, devices, and methods described herein address the disadvantages in the conventional art.

I. Sensor Systems and Devices

A. Advantages Over Known Techniques

The sensors described here may provide many advantages relative to conventional sensors using, for example, a known Wheatstone Bridge. Examples of these advantages include but are not limited to the following.

First, the sensors (e.g., pressure, force) described herein may utilize a MEMS circuit arrangement in which an analog-to-digital conversion may be performed directly on a sensor die. In some variations, rather than have a very small differential voltage as the output, sensors described herein may produce a digital output (e.g., a serial digital stream), such as a standard universal asynchronous receiver transmitter (UART), that may be easily read directly by a compute device, such as an off-the-shelf microcontrollers. Second, use of the sensors described herein may reduce manufacturing costs, system sizes, and system power, and may allow for increased flexibility in how devices utilizing these sensors (e.g., medical devices) are prototyped, designed, and manufactured. Space and power consumption may be important considerations for some pieces of equipment carried into austere settings. The development of fully digital pressure sensors, such as those described herein, greatly simplifies the backend electronics for these devices. For example, at least because the sensors described herein may use, in some variations, power and a precise clock as inputs, the compute device may be greatly simplified compared to known techniques: just a power source, a clock source, and a circuit to receive a serial message (e.g., UART) and convert it to a wired or wireless format. That way, in some variations, the display could be separated by any arbitrary distance. Also, because the sensor is inherently always in "output mode" (rather than read-response mode), the output values may be sent to more than one compute devices.

Third, as will be discussed in more detail herein, the sensors described may provide a digital output (e.g., a serial digital stream indicating pressure), which may allow for disconnection of portions of a device (e.g., in the context of a medical device comprising an elongate body such as a catheter, the catheter shaft) from external electronics, so that the electronics are usable with multiple devices. Moreover, the sensors described herein also allow for replacement of portions of the electronics in the event the electronics are damaged and/or out of power. In variations in which the sensors described herein are utilized in a medical device (e.g., a blood flow regulation device), a portion of the medical device advanced into a patient may remain in the patient while the external electronics (e.g., compute device) are replaced.

Fourth, the sensors described herein may provide higher quality digital outputs than conventional Wheatstone bridge sensors providing analog signals. For example, with respect to use in a pressure sensing application in particular, the digital outputs may have, for example, at least times greater noise tolerance than analog signals. As one example, if the digital output is nominally 3.3V for a logic 1 and 0V for a logic 0, a receiver may be capable of tolerating, for example, a noise level of 1V and still distinguish between a 1 or 0. For the analog-based Wheatstone bridge, a noise level of only 100 microvolts might correspond to as much as 4 mmHg of change in the pressure reading. This may be too much error for high fidelity physiologic monitoring that may form the basis of medical devices. In addition, digital messaging schemes increase signal fidelity by also allowing for addition of error detection bits that may further improve confidence that the received message has not been corrupted. Additionally, in some variations, such as those in which a compute device receives a digital value, the temperature of the compute device may have little or no effect and no compensation or calibration may be needed for the circuit generating the digital value. Also, having a digital output from the sensor may eliminate the amplification stage that has previously been used for analog solid state pressure sensors or with fluid-column based pressure sensors. Since there is no analog amplifier, there is also no need to match the voltages between the amplifier and associated ADC.

Fifth, in some variations, the sensors described herein utilize sensor wires that may be immune, or less susceptible to, RF-induced noise. For example, the sensors described herein may utilize sensor wires that are smaller than conventional sensor wires (e.g., <0.1 mm), and thus the sensor wires may be too small to be susceptible to RF-induced noise.

Moreover, having only digital signals traversing the long wires eliminates the need for almost all of the low-pass filters. This may save space on the sensor circuit, reduce complexity, and/or the like.

Sixth, the sensors described herein are easily adaptable across a variety of silicon processes compared to known techniques, thus allowing them to be versatile across processes.

Seventh, the sensors described herein may provide improved fault detection compared to conventional sensing techniques. For example, if any of the sensor wires are damaged, the compute device (e.g., microcontroller) may detect the failure within a short time frame (e.g., 1 sample period), since digital outputs from the sensor will cease.

Eighth, the sensors described herein easily allow for the use of various runtime diagnostics by varying the input clock rate or varying the supplied voltage, which is not possible in many conventional sensing techniques.

While there are many advantages to utilizing the sensors described herein, there may also be challenges in creating a sensor with a built-in analog-to-digital converter (ADC). It may be desirable, for example, for the ADC to add minimal size to the silicon die so that the ADC still fits within the size constraints of the device for the particular application, such as, for example, within an elongate body in a medical device. It may also be desirable, for example, for the sensing element and the ADC be tolerant to voltage variations, since, in some implementations, the sensor die may be at least 50-100 cm away from the power supply. It may also be desirable, for example, for the ADC to be tolerant to variations in sensor location (such as, for example, inside a patient) or temperature.

Some known analog-to-digital conversion is performed using sigma-delta or successive approximation techniques. This may require complex circuits that must be adapted for each silicon process, and may be sensitive to the operating voltage and temperature. Some variations, as will be shown and discussed with respect to FIGS. 11A and 11B, use an approach for generating a digital output from the essentially analog sensor measurement. For example, some variations use a set of oscillating rings, a set of counters and latches, and some mathematical calculations to perform the analog to digital conversion, as will be discussed in more detail herein.

B. Sensor Systems

Figure 3:
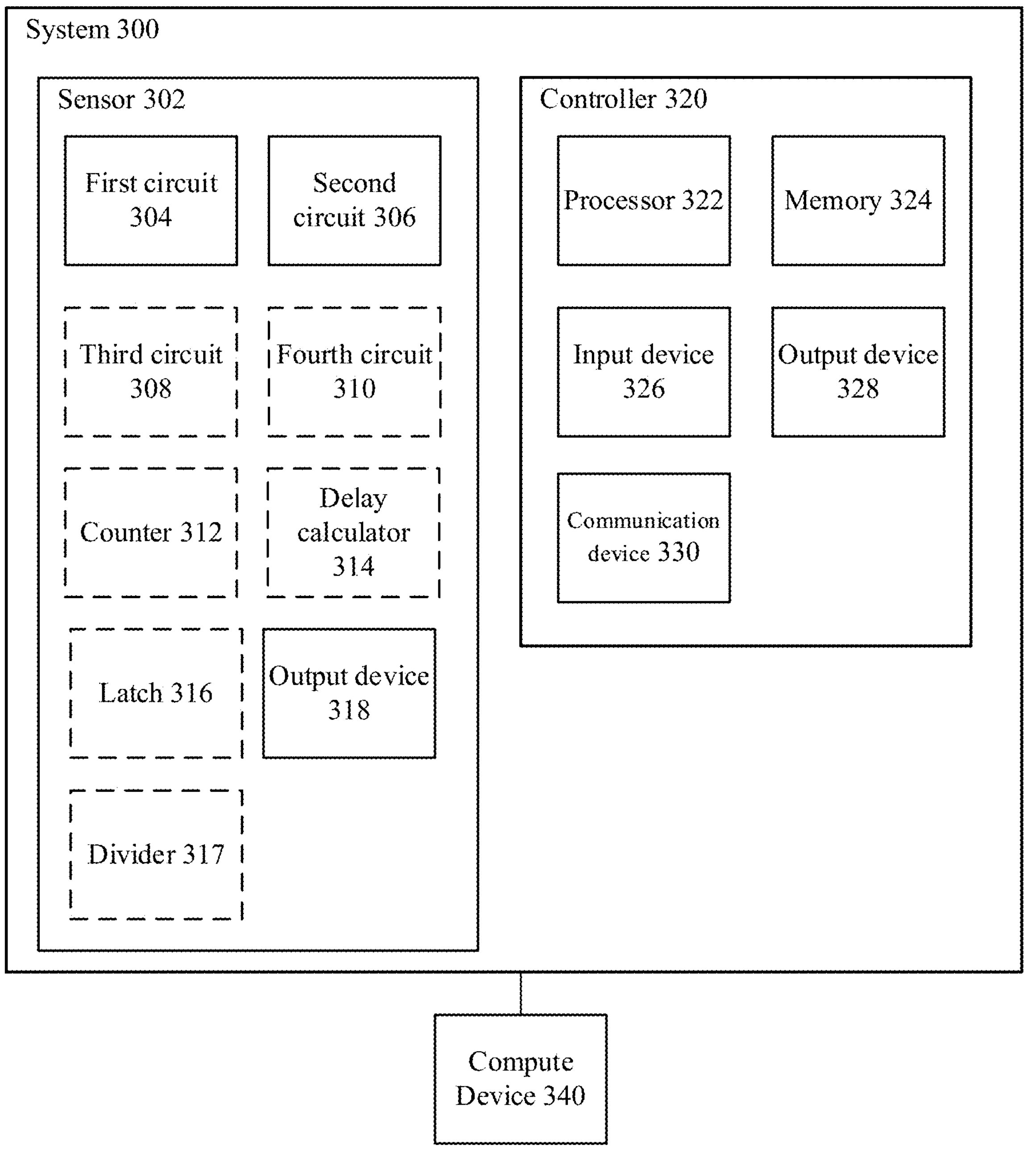
FIG. 3 is a schematic block diagram an illustrative variation of a sensor system.

Generally, a sensor system may include one or more of the components necessary to measure and optionally output a parameter using the systems as described herein. A block diagram of an exemplary solid state sensor system 300 is depicted in FIG. 3. The system 300 may comprise one or more of a sensor 302, a controller 320 (e.g., device controller, microcontroller), and a compute device 340. In some variations, the sensor 302 may be coupled to one or more of the controller 320 and the compute device 340 via a network (e.g., via a wired or wireless connection). The sensor 302 may be configured to measure one or more parameters (e.g., temperature, voltage, force, pressure, light amplitude, audio amplitude, radiation). The measured parameter may correspond to any parameter capable of varying a time delay of a delay element. For example, one or more of resistance, capacitance, and inductance may be varied in response to a variation in a parameter. In some variations, a measured parameter may be based on another circuit (e.g., resonator) coupled to an oscillator ring such that the measured parameter is based on a second order approach. In some variations, the system 300 may be configured to output the sensor measurements via the controller 320. For example, the controller 320 may be configured to output a digital signal (e.g., of the measured parameter) to a compute device 340 without analog to digital conversion. In this manner, the system 300 may be formed absent an ADC, which may reduce one or more of the size, cost, and manufacturing complexity of the system 300.

Referring back to FIG. 3, in some variations, the sensor system 300 may comprise one or more of a sensor 302 and a controller 320. The sensor 302 may comprise one or more of a first circuit 304, a second circuit 306, an optional third circuit 308, an optional fourth circuit 310, an optional rate counter 312, an optional delay calculator 314, an optional latch 316, an optional divider 317, and an output device 318. In some variations, one or more of the first circuit 304, the second circuit 306, the third circuit 308, and the optional fourth circuit 310 may comprise a ring oscillator circuit as described in more detail herein. In some variations, the divider 317 may include one or more sets of circuitry configured to divide an input signal (e.g., convert a 32,768,000 Hz clock to a 16,384,000 Hz clock). In some variations, the counter 312 may include one or more sets of circuitry configured to count the number of oscillations (i.e., ticks) at the first circuit 304, second circuit 306, third circuit 308, and/or fourth circuit 310 during a sample period(s). In some variations, the latch 316 may include one or more sets of circuitry configured to store representations of counts captured by the counter 312. In some variations, the output device 318 may be configured to transmit a signal(s) indicating counts captured by the counter 312 and/or stored in the latch 316. In some variations the output device 318 may include a shift register, output register, serializer, and/or the like.

The controller 320 may comprise one or more of a processor 322, a memory 324, an input device 326, an output device 328, and a communication device 330, each of which are described in more detail herein. In some variations, the system 300 may be disposed on a single substrate (e.g., single die) or on a plurality of substrates. For example, the sensor 302 may be disposed on a first substrate and the controller 320 may be disposed on a second substrate.

In some variations, the input device 326 may be configured to receive a signal based on a set of output clock signals from the sensor 302. In some variations, the output device 326 may be configured to output data associated with the system 300 as a digital signal. In some variations, the processor 322 and memory 324 may be configured to control the sensor system 300. In some variations, the communication device 330 may be configured to communicate with one or more components of the system 300 and the compute device 340 (e.g., mobile phone, tablet, laptop, desktop PC). In some variations, compute device 340 is a microcontroller.

Note that, although FIG. 3 shows the compute device 340 as being separate from the controller 320, in some variations, the controller 320 and the compute device 340 may be a single unit (e.g., a single chip).

In some variations, multiple sensors may be coupled to one another. For example, in some variations, a plurality of sensors (two, three, four, or more) may be coupled serially to one another (i.e., daisy chained). In these variations, the clock rate may be modified to account for the daisy chained sensors. As an example, if a 32,768 Hz input clock may have been used for measuring a value from a single sensor, the clock rate in a daisy chained variation may be 32,768 Hz multiplied by the number of sensors in the daisy chain (e.g., use a 65,536 Hz clock if two sensors are daisy chained, use a 98,304 Hz clock if three sensors are daisy chained, etc.). Additionally an input may be added to the serializer (i.e., shift register) that receives bits from the upstream sensor(s), as shown at FIG. 14B. Therefore, the digital output (e.g., UART-style serial out) may report the value from the multiple latches inside multiple sensor chips to a compute device. In some variations, multiple sensors may be read using just 4 wires to/from the compute device: the power, ground, and clock wires may each couple to all sensors, and the output of each sensor may couple to the "shift in" of the subsequent sensor until the final sensor in the chain produces a digital output that may couple to, for example, a UART input of a compute device.

Figure 14A:
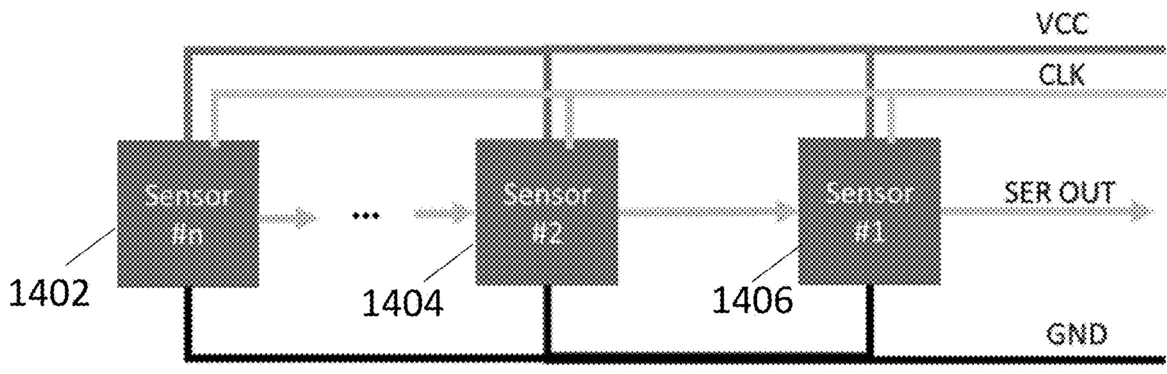
FIGS. 14A and 14B show an exemplary configuration of multiple sensors that are connected in series (e.g., daisy chained together), and a latching serializer that receives bits from an upstream sensor to generate a serial output measured by the connected sensors, respectively.
Figure 14B:
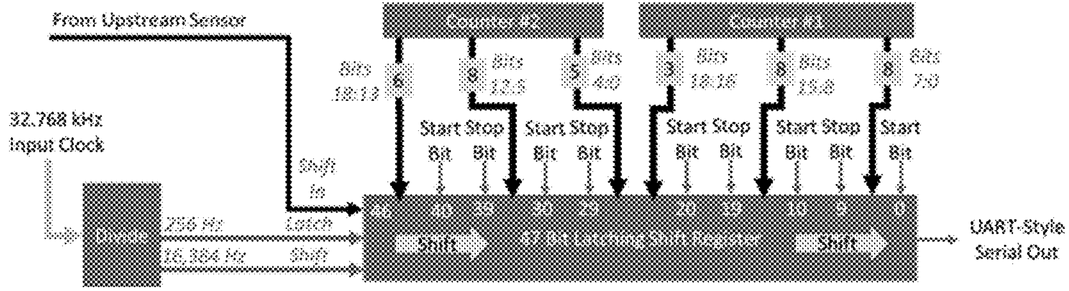

An example of daisy chained sensors is shown in FIG. 14A. A first sensor 1402 may measure a first value, the first value may be provided to (e.g., as input to the serializer of) a second sensor 1404 that may measure a second value, the second value may be provided to (e.g., as input to the serializer of) a third sensor 1406 that may measure a third value, and a digital output ("SER OUT") may be produced that is a serial listing of each of the values measured by each of the sensor 1402, 1402, and 1406. In some variations, each value measured by each sensor gets concatenated to input provided to the serializer of that sensor (if an input was provided for that sensor). For example, "SER OUT" may be a list of bits that indicate bits representing the value measured by sensor 1402, followed by bits representing the value measured by sensor 1404, followed by bits representing the value measured by sensor 1406. In some variations, each value measured by each sensor is separated by other values measured by other sensors using a known indicator, such as a predetermined combination of bits known by a processor. "SER OUT" may be provided to a compute device configured to then identify each value measured by each sensor using "SER OUT." Sensor 1402, 1404, and 1406 may all measure the same parameter (e.g., pressure), all measure different parameters (e.g., pressure, force, light amplitude), or a combination of some sensors measuring the same parameter and some sensors measuring different parameters. As shown in FIG. 14A, the daisy chain of sensors may only have 4 wires—the voltage (VCC), the clock (CLK), the serial output (SER OUT), and the ground (GND). In one example, the sensor may be placed within a human, and the 4 wires may be connected to a compute device (e.g., a microcontroller) further away (e.g., 50 to 100 cm away) from the sensor and configured to determine each value measured by sensors 1402, 1404, and 1406. Using a variation similar to FIG. 14A may allow a single UART to read multiple sensors, and may also greatly reduce the total number of wires to route within a system that has many sensors (e.g., since only one SER OUT for the plurality of sensors rather than each sensor having its own SER OUT).

Figure 15:
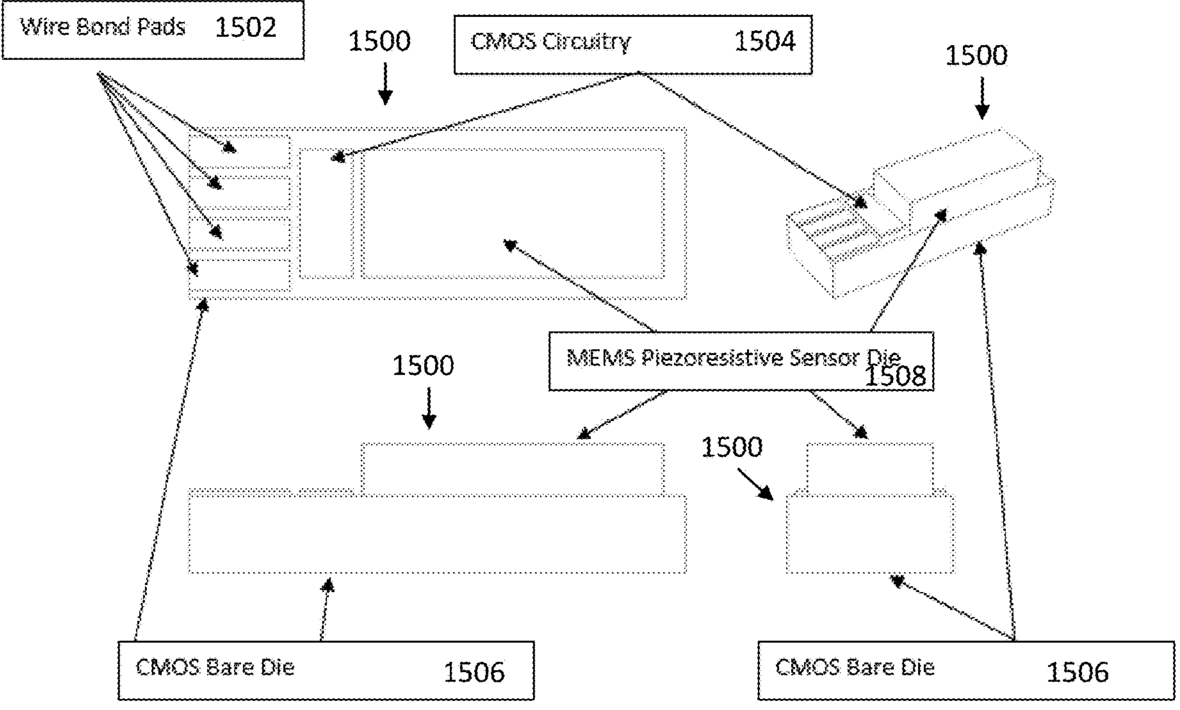
FIG. 15 shows a top, perspective, side, and front view of an exemplary variation of a chip.

FIG. 15 shows a top view, a side view, a front view, and a perspective view of an exemplary chip. The chip 1500 can include a sensor. As shown there, the chip 1500 may include a plurality of wire bond pads 1502 positioned above a complementary metal-oxide semiconductor (CMOS) bare die 1506. More specifically, the chip 1500 may include four bond pads, one each for the voltage, the clock, the serial output, and the ground, and the wire bond pads 1502 may be positioned on a top surface of the CMOS bare die 1510. The chip 1500 may further include a sensor delay—a micro-electromechanical systems (MEMS) piezoresistive sensor die 1508. The MEMS piezoresistive sensor die 1508 may be configured to delay the number of oscillations by one or more ring circuits based on a parameter to be measured (e.g., pressure). The chip 1500 may further comprise CMOS circuitry 1504, which may include the remaining sensor components (e.g., oscillator rings, latch, counter, serializer). In some variations, as will be discussed herein, the chip 1500 may be placed within a sensor housing. In some variations, the CMOS bare die 1506 may have a width of about 200 microns to about 500 microns, about 250 microns to about 450 microns, a width of about 300 microns to about 400 microns, a width of about 330 microns, a width less than 200 microns, and/or a width greater than 500 microns (including all values and sub-ranges therein). In some variations, each wire bond pad from wire bond pads 1502 may have a width of about 20 to about 100 microns or about 30 to about 90 microns (including all values and sub-ranges in any of the foregoing), and/or a length of about 150 to about 250 microns or about 175 to about 225 microns (including all values and sub-ranges in any of the foregoing). In other variations, each wire bond pad from wire bond pads 1502 may have a width less than 20 microns, a width greater than 100 microns, a length less than 150 microns, and/or a length greater than 225 microns. In further variations, the CMOS circuitry 1504 may have a width of about 200 to about 300 microns or about 225 to about 275 microns (including all values and sub-ranges in any of the foregoing), and/or a length of about 50 to about 150 microns or about 75 to about 125 microns (including all values and sub-ranges in any of the foregoing). Alternatively, the CMOS circuitry 1504 may have a width less than 200 microns, a width greater than 300 microns, a length less than 50 microns, and/or a length greater than 125 microns. In yet further variations, the MEMS piezoresistive sensor 1508 may have a width of about 200 to about 300 microns or about 225 to about 275 microns (including all values and sub-ranges in any of the foregoing), a length of about 500 to about 700 microns or about 550 to about 650 microns (including all values and sub-ranges in any of the foregoing), and/or a height of about 200 to about 300 microns or about 225 to about 275 microns (including all values and sub-ranges in any of the foregoing). In some variations, the MEMS piezoresistive sensor 1508 has a width less than 200 microns, a width greater than 300 microns, a length less than 500 microns, a length greater than 700 microns, a height less than 200 microns, and/or a height greater than 300 microns.

Figure 16:
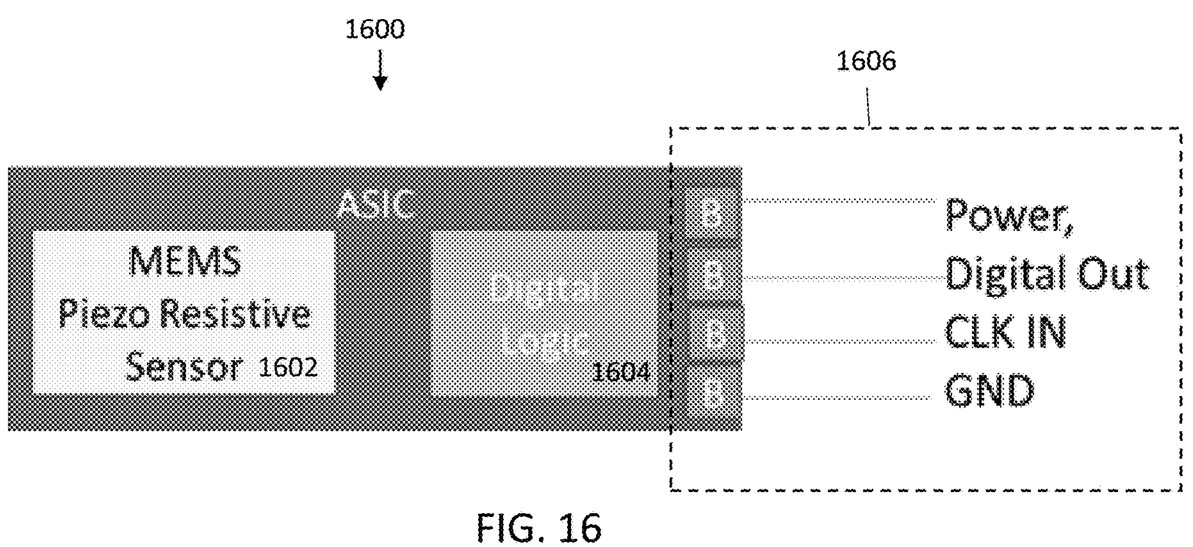
FIG. 16 shows an exemplary block diagram of a sensor.

In some implementations, a sensor (e.g., included in chip 1500) may be incorporated at an application-specific integrated circuit (ASIC). For example, FIG. 16 shows a block diagram of an exemplary sensor 1600 incorporated at an ASIC. As shown there, the sensor 1600 may include a plurality of wire bond pads 1606 (e.g., 4 wire bond pads), similar to the wire bond pads 1502 depicted in the sensor of FIG. 15. These 4 wire bond pads may be operatively coupled to digital logic 1604 configured to oscillate multiple rings, and count the number of oscillations for each of these rings. The sensor 1600 may also include a MEMS piezo resistive sensor 1602 that may be configured to delay, via resistance, the number of oscillations at a first oscillating ring (but not at a second oscillating ring) based on a parameter value that is to be measured.

a. Oscillator Circuit

Generally, the oscillator circuits (e.g., compensated ring oscillator) described herein may be configured to receive an input clock signal and generate an output clock signal having a frequency greater than the input clock signal. The oscillator circuit may comprise one or more (e.g., a plurality) of delay circuits (e.g., inverter circuits, such as Schmidt-trigger inverters) arranged in a ring configuration. The oscillator circuit may be configured to generate an output clock signal having a predetermined ratio (e.g., output clock signal is an integer multiple of the input clock signal) by compensating for inherent circuit offsets such as temperature and voltage by adjusting a delay of the oscillator circuit. Circuits suitable for use in the systems, devices, and methods here are described in U.S. Pat. No. 6,911,872, filed Mar. 25, 2003, granted Jun. 28, 2005, and titled "Circuit and Method for Generating a Clock Signal," which is hereby incorporated by reference in its entirety.

Figure 4:
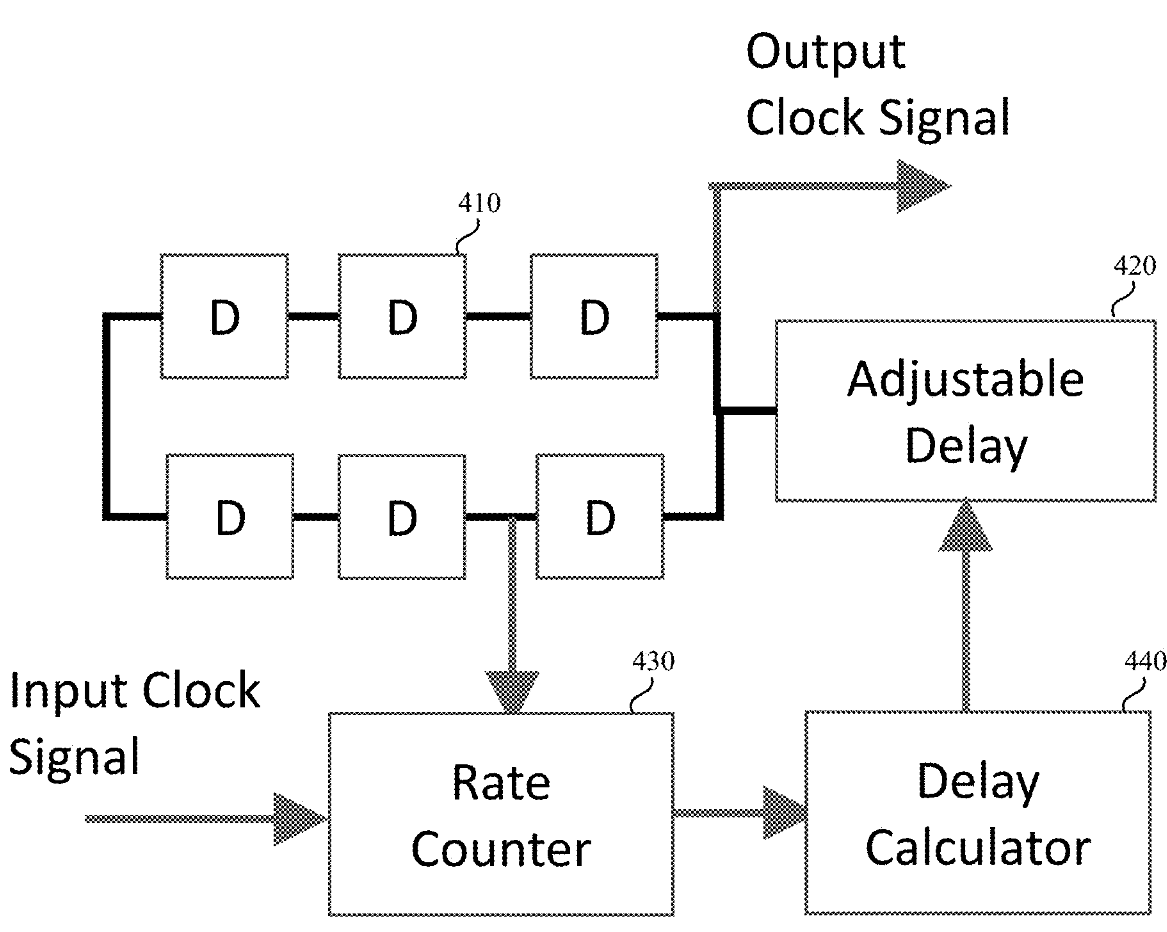
FIG. 4 is a schematic diagram of an illustrative variation of an oscillator circuit.

FIG. 4 is a schematic diagram of an illustrative variation of an oscillator circuit 400 comprising a plurality of delay circuits 410 and an adjustable delay circuit 420 arranged in a ring configuration, a rate counter circuit 430, and a delay calculator circuit 440. The circuit 400 is configured to receive an input clock signal and generate an output clock signal having a predetermined ratio between the input clock signal and the output clock signal using an adjustable delay circuit 420 calculated by the delay calculator circuit 440. The adjustable delay circuit 420 may be configured to set a predetermined delay based on the calculated adjustable delay. That is, the adjustable delay may be calculated by comparing a ratio of the output clock signal (e.g., ring frequency) to the input clock signal, and adjusting the adjustable delay to the predetermined ratio. In some variations, the adjustable delay circuit 420 comprises one or more of a resistor-capacitor delay circuit, a resistor-inductor delay circuit, and a capacitive delay circuit.

The rate counter circuit 430 may be configured to count the number of output clocks that occur for each single count of the input clock. The delay calculator circuit 440 may be configured to calculate a difference between the output of the rate counter circuit 430 and the predetermined ratio.

A frequency of the output clock signal may be greater than a frequency of the input clock signal. In some variations, the plurality of delay circuits 410 may be coupled to a multiplexer (not shown). In some variations, a first plurality of inverter circuits may be configured in a closed loop with positive feedback. In some variations, the oscillator circuit 400 may be disposed on one or more substrates (e.g., silicon dies).

An exemplary operation the oscillator circuit 400 is described below. For a predetermined ratio of 1000 and a rate counter value of 998 output clock counts for every one input clock counts, the delay calculator circuit 440 may calculate and set an adjustable delay to run slower by 2 counts per input clock using the adjustable delay circuit 420. As another example, an input clock signal having a frequency of 32,768 Hz and a predetermined ratio of 1000 corresponds to an output clock signal having a frequency of 32,768,000 Hz. Accordingly, the total delay of the ring may be about 30.52 ns (1/32,768,000). If the propagation time of the individual delay circuit (e.g., inverter circuit) is about 50 picoseconds, then the oscillator circuit may comprise about 61 delay circuits. It should be appreciated that input clock signals having a frequency of 32.768 kHz, for example, may have high precision as they are based on large quartz crystals cut to precise sizes. For example, crystals used in digital watches and computer systems typically achieve accuracies in the range of +/−10 ppm (+/−0.001%) or better. Furthermore, these input clock signals may be transmitted over relatively long distances while retaining immunity to noise. In some variations, the input clock signal may have a frequency of 32,768 Hz, or an integer fraction of that rate (e.g., 16,384 Hz, 8,192 Hz, etc.).

For silicon-based implementations, the oscillator circuit 400 compensates for variations in temperature, voltage, and the inherent speed of a silicon substrate. For example, an increase in temperature corresponds to an increase in propagation time through the delay elements and a slower output clock signal. Conversely, an increase in voltage corresponds to a shorter propagation delay and a faster output clock signal. In some variations, the adjustable delay circuit 420 may comprise a range sufficient to compensate for the variation of propagation delays within an individual silicon process. For example, a substrate (e.g., silicon die) from one manufacturing lot may have propagation delays that vary by up to about 20% from another substrate from another manufacturing lot, even though both substrates were subjected to the same voltage and temperature. The differences in the silicon from manufacturing lot to manufacturing lot are sometimes called the "silicon skew".

Figure 5:
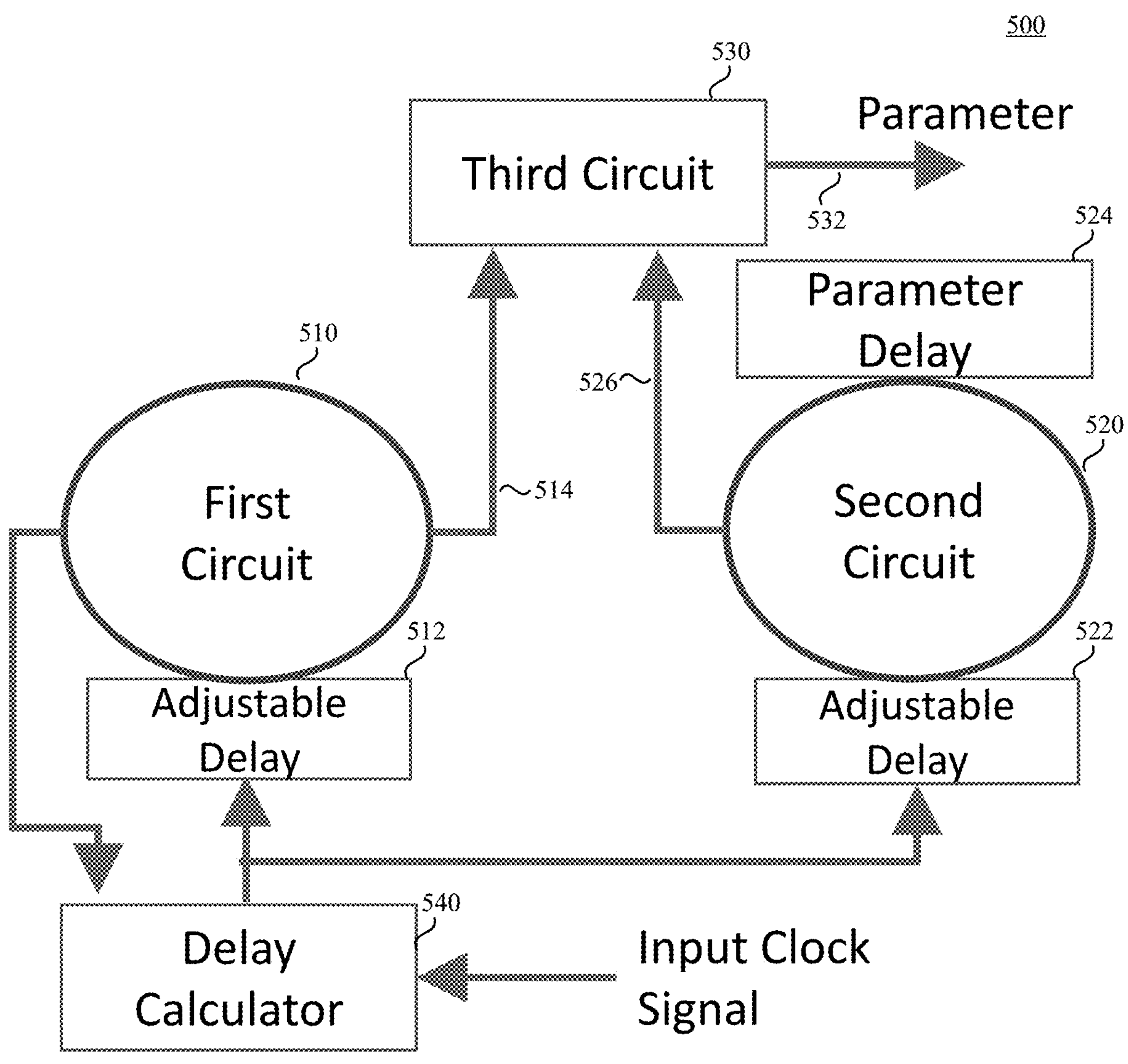
FIG. 5 is a schematic diagram of an illustrative variation of a sensor.

FIG. 5 is a schematic diagram of an illustrative variation of a sensor comprising a plurality of oscillator ring circuits. For example, the sensor 500 may comprise a first circuit 510, a second circuit 520, a third circuit 530, and a delay calculator circuit 540. Each of the first circuit 510 and the second circuit 520 may comprise a plurality of delay circuits arranged in a ring configuration and a rate counter circuit similar to those shown and described with respect to FIG. 4. Furthermore, the first circuit 510 may comprise a first adjustable delay circuit 512 and the second circuit 520 may comprise a second adjustable delay circuit 522. The first circuit 510 and the second circuit 520 may be configured to receive an input clock signal and generate respective output clock signals having a predetermined ratio between the input clock signal and the output clock signal using respective adjustable delay circuits 512, 522 calculated by the delay calculator circuit 540. The adjustable delay circuits 512, 522 may be configured to set a predetermined delay based on the calculated adjustable delay. That is, the adjustable delay may be calculated by comparing a ratio of the output clock signal of the first circuit 510 to the input clock signal, and adjusting the adjustable delay of both the first circuit 510 and the second circuit 520 to the predetermined ratio. The delay calculator circuit 540 may be configured to calculate a difference between the output of the rate counter circuit of the first circuit 510 and the predetermined ratio. A frequency of the first output clock signal 510 and the second output clock signal 526 are each greater than a frequency of the input clock signal.

In some variations, the first circuit 510 may comprise a first oscillator circuit (similar to oscillator circuit 400). Similarly, the second circuit 520 may comprise a second oscillator circuit. The first circuit 510 may be configured to receive an input clock signal and output a first output clock signal 514 having a predetermined ratio between the input clock signal and the first output clock signal 514 using an adjustable delay. In some variations, the second circuit 520 may be configured to receive the input clock signal and output a second output clock signal 526 using the adjustable delay. In some variations, the third circuit 530 may be coupled to the first circuit 510 and the second circuit 520, and the third circuit 530 may be configured to generate a third signal 532 based on a difference between the first output clock signal 514 and the second output clock signal 526. The third signal 532 may correspond to a measured parameter. For example, third signal 532 may correspond to one or more of temperature, voltage, force, pressure, light amplitude, and audio amplitude. In some variations, the third signal 532 may be processed to output a parameter signal corresponding to a unit of measurement (e.g., mmHg).

In some variations, the first circuit 510 comprises a first plurality of delay circuits arranged in a ring configuration. The first plurality of delay circuits may comprise a first plurality of inverter circuits and a first adjustable delay circuit 512. The first adjustable delay circuit 512 may comprise a first rate counter. The first plurality of inverter circuits may be coupled to a first multiplexer. The first plurality of inverter circuits may be configured in a closed loop with positive feedback. The first delay circuit may comprise a first resistor-capacitor delay circuit.

The first output clock signal 514 may vary based on a first set of parameters and the second output clock signal 526 may vary based on a second set of parameters different from the first set of parameters. For example, the first set of parameters may comprise one or more of temperature and voltage. In some variations, the second set of parameters may comprise temperature, voltage, and one or more of force, pressure, light amplitude, audio amplitude, and resistance or capacitance corresponding to a chemical or physical reaction. That is, the second set of parameters may include the first set of parameters and at least one additional parameter.

In some variations, the third signal 532 may be processed to calculate a difference in the second output clock signal 516 relative a starting condition (e.g., tare). For example, a tare signal may be provided as a separate input or as a signal using an in-band encoding on the input clock signal.

In some variations, the second circuit 520 comprises a second plurality of delay circuits arranged in a ring configuration. The second plurality of delay circuits may comprise a second plurality of inverter circuits and a second adjustable delay circuit 522. The second adjustable delay circuit 522 may comprise a second rate counter. The second plurality of inverter circuits may be coupled to a second multiplexer. The second plurality of inverter circuits may be configured in a closed loop with positive feedback. The second adjustable delay circuit 522 may comprise one or more of a resistor-capacitor delay circuit, a resistor-inductor delay circuit, and a capacitive delay circuit. The second circuit 520 may comprise at least one delay circuit configured to vary based on at least one additional parameter different than the first circuit 510.

In some variations, the second plurality of delay circuits may comprise the same delay circuits as the first set of delay circuits and at least one additional delay circuit configured to vary based on a parameter to be measured (e.g., pressure). In this manner, the output clock signals 514, 526 from the respective first circuit 510 and second circuit 520 may differ as the parameter to be measured (e.g., pressure) changes. In variations where the first circuit 510 and the second circuit 520 are disposed on the same substrate (e.g., same silicon die), an adjustable delay due to temperature and voltage offsets will be the same for the first circuit 510 and the second circuit 520. Thus, a difference between first output clock signal 514 and the second output clock signal 526 will be due to changes in the measured parameter (e.g., pressure) and independent of offsets such as temperature, voltage, and silicon skew. In some variations, the additional delay circuit of the second circuit 520 may comprise one or more of a resistor-capacitor delay circuit, a resistor-inductor delay circuit, and a capacitive delay circuit. Any physical property (e.g., pressure, force, light amplitude, audio amplitude, voltage) that may result in a change in electrical propagation time (e.g., delay) may be measured in this manner. For example, the sensor 500 may be used for electrochemical analysis where a chemical reaction results in a change in the resistance or capacitance. The systems, devices, and methods described reduce circuit complexity and size by avoiding precision current sources and voltage measurement ADCs.

In some variations, the sensor 500 may be disposed on one or more substrates (e.g., silicon dies). For example, a single substrate may comprise the first circuit, the second circuit, and the third circuit. In other variations, a first substrate may comprise one of the first circuit and the second circuit, and a second substrate may comprise the other of the first circuit and the second circuit. Furthermore, each circuit of the sensor 500 may be disposed on its own substrate or any combination of substrates.

An exemplary operation the oscillator circuit 500 is described below. For an input clock signal having a frequency of 32,768 Hz and a first output clock signal having a frequency of 32,768,000 Hz, a predetermined sample rate of 200 Hz (e.g., 5 millisecond sample period), a span of 1000 mmHg pressure (min to max), a predetermined resolution of 0.25 mmHg, 4,000 quantized levels are required (1,000 mmHg/0.25 mmHG=4,000 quantized levels). In this case, the second circuit 520 may have about 163,840 clocks per 5 ms sampling period. One clock period is 1/32,768,000 second (30.52 ns). Therefore, the delay varies by 30.52 ns for each 0.25 mmHg of pressure. It should be appreciated that the 4,000 quantized levels is much less than the 163,840 clocks each 5 millisecond period such that the count may be measured using a digital counter. If a sensor measurement requires more than 30.52 ns for each 0.25 mmHg of pressure, then a faster clock rate may be used. Conversely, if the variation in delay is more than 30.52 ns for each 0.25 mmHg of pressure, then a slower clock may be used.

In some variations, an optional fourth circuit (e.g., fourth circuit 310 in FIG. 3) may be configured to measure a parameter different from the second circuit 520. For example, the fourth circuit may comprise a delay circuit configured to vary based on temperature. The fourth circuit may have a configuration similar to the second circuit 520 described herein.

In some variations, a fourth circuit may be coupled to the third circuit. The fourth circuit may be configured to receive the input clock signal and output a fourth output clock signal using the adjustable delay. The third circuit may be configured to generate a fifth signal based on a difference between the first output clock signal and the fourth output clock signal. The fifth signal corresponds to one or more of temperature, voltage, force, pressure, light amplitude, and audio amplitude. In this manner, the sensor 500 may be configured to measure a plurality of parameters while compensating for offsets without offset compensation circuits.

In some variations, the sensor 500 may be powered by a set of three wires: a first wire associated with a positive voltage, a second wire associated with a ground, and a third wire associated with a input clock signal (which may be referenced to the ground). In some variations, power may be derived only from the input clock signal.

In some variations, the sensors described herein may be disposed on a 50 nm process including about 5,000 gates and about 10,000 gates/$mm^2$. In some variations, a die may comprise a size of more than about 0.3 $mm^2$. In some variations, the sensor 500 may comprise a low-pass filter to reduce noise on the power supplied to the delay elements (e.g., noise above 16.384 kHz corresponding to a Nyquist rate of a 32.768 kHz crystal).

Figure 9A:
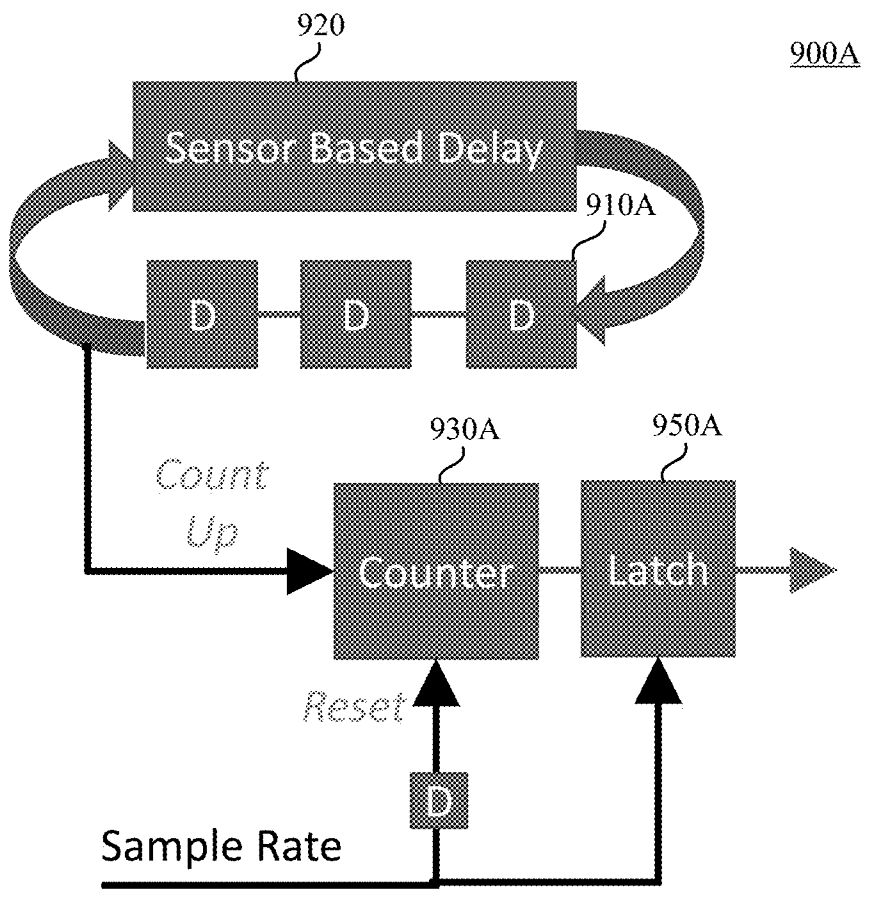
FIGS. 9A and 9B show a schematic diagram of a first ring oscillator circuit and a second ring oscillator circuit, respectively.
Figure 9B:
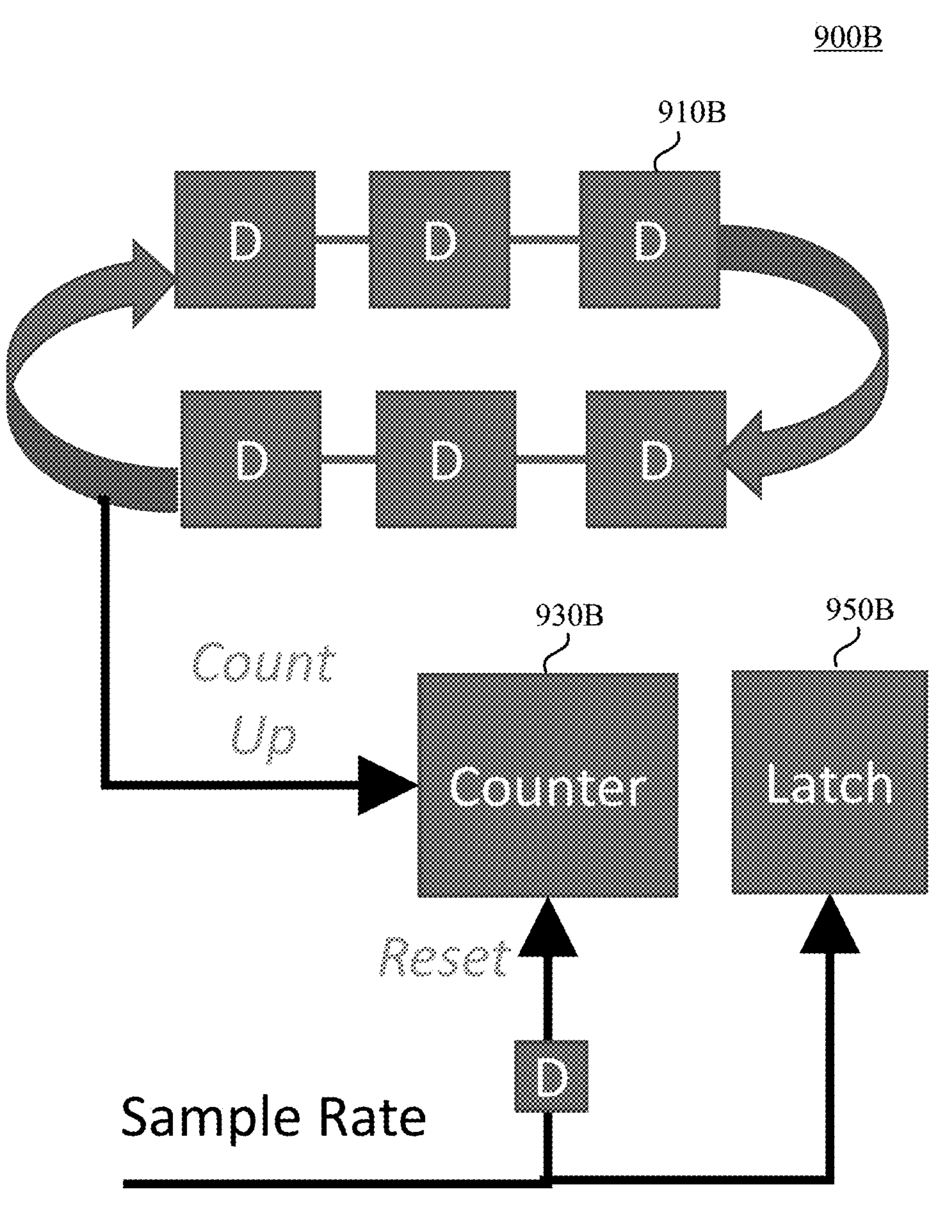

FIGS. 9A and 9B show schematic diagrams of two different ring oscillator circuits that may be used in combination to provide respective count values, where count values from the two different ring oscillator circuits may be used to determine the value of a parameter(s) of interest (e.g., pressure, force, light amplitude, audio amplitude, radiation, resistance or capacitance corresponding to a chemical or physical reaction, etc.). FIG. 9A shows a schematic diagram of an oscillator circuit 900A comprising a set of delay circuits 910A and a parameter-based delay circuit 920 arranged in a ring configuration (i.e., a first ring circuit), a rate counter circuit 930A (i.e., counter), and a latch circuit 950A (i.e., latch). Delay of the parameter-based delay circuit 920 varies based on the parameter(s) of interest (e.g., more delay as pressure decreases, less delay as pressure increases, etc.). FIG. 9B shows a schematic diagram of an oscillator circuit 900B comprising a set of delay circuits 910A arranged in a ring configuration (i.e., a second ring circuit), a rate counter circuit 930B, and a latch circuit 950B. The oscillation rate of the second ring circuit will vary based on a first set of parameters (e.g., temperature and voltage) not including the parameter(s) of interest, while the oscillation rate of the first ring circuit will vary based on the first set of parameters and the parameter(s) of interest. Oscillator circuit 900A may function similar to a measurement circuit for determining a tentative predicted value(s) for a parameter(s) of interest, and oscillator circuit 900B may function similar to a calibration circuit for adjusting the tentative predicted value(s) by compensating for variations potentially caused by the first set of parameters.

Referring to FIG. 9A, the oscillation rate of the first ring circuit may be sampled at a first sample rate (i.e., predetermined sample rate), and the rate counter circuit 930A and the latch circuit 950A may be used to count and store, respectively, the number of oscillations of the first ring circuit during each sample period (e.g., at each rising edge of the sample rate clock). For example, if the first ring circuit is oscillating at 100 MHz and the sample rate is 256 Hz (approximately 1 sample every 4 ms), the rate counter circuit 930A will count approximately 400,000 oscillations of the first ring circuit every 4 ms. For each sample period, the latch circuit 950A may receive an output count signal, and store a representation of the count value counted by the rate counter circuit 930A at that sample period for future processing (as indicated in the output count signal). As previously mentioned, the number of oscillations at the first ring circuit may vary across sample period based on the first set of parameters and at least one additional parameter (i.e., the parameter of interest). Thus, output of the latch circuit 950A may be a near continuous characterization of the first ring circuit's behavior relative to the first set of parameters and the parameter(s) of interest. In some variations, the delay circuits 910A may include a set of inverters; in some variations, the set of inverters may be coupled to a multiplexer. In some variations, the set of inverters are configured in a closed loop with positive feedback. In some variations, the first ring circuit may include one or more of a resistor-capacitor delay circuit, a resistor-inductor delay circuit, and a capacitive delay circuit.

Referring to FIG. 9B, the oscillation rate of the second ring circuit may be sampled at a second sample rate (i.e., predetermined sample rate), and the rate counter circuit 930B and the latch circuit 950B may be used to count and store, respectively, the number of oscillations of the second ring circuitry during each sample period. As previously mentioned, the number of oscillations at the second ring circuit may vary across sample periods based on the first set of parameters, but not the parameter(s) of interest, since the second ring circuit does not include a parameter-based delay circuit. Thus, output of the latch circuit 950B may be a near continuous characterization of the second ring circuit's behavior relative to the first set of parameters. In some variations, the second ring circuit oscillates at a rate between 30-60 MHz (e.g., +/−20% from die to die, +/−20% based on voltage and temperature, etc.). In some variations, multiple sample periods may be averaged (e.g., total count of oscillations for a range of sample periods/number of sample periods in the range of sample periods), such as, for example, if the first set of parameters includes temperature, since temperature generally changes relatively slowly relative to the sample rate. In some variations, the delay circuits 910B may include a set of inverters; in some variations, the set of inverters may be coupled to a multiplexer. In some variations, the set of inverters are configured in a closed loop with positive feedback. In some variations, the second ring circuit may include one or more of a resistor-capacitor delay circuit, a resistor-inductor delay circuit, and a capacitive delay circuit.

Figure 10:
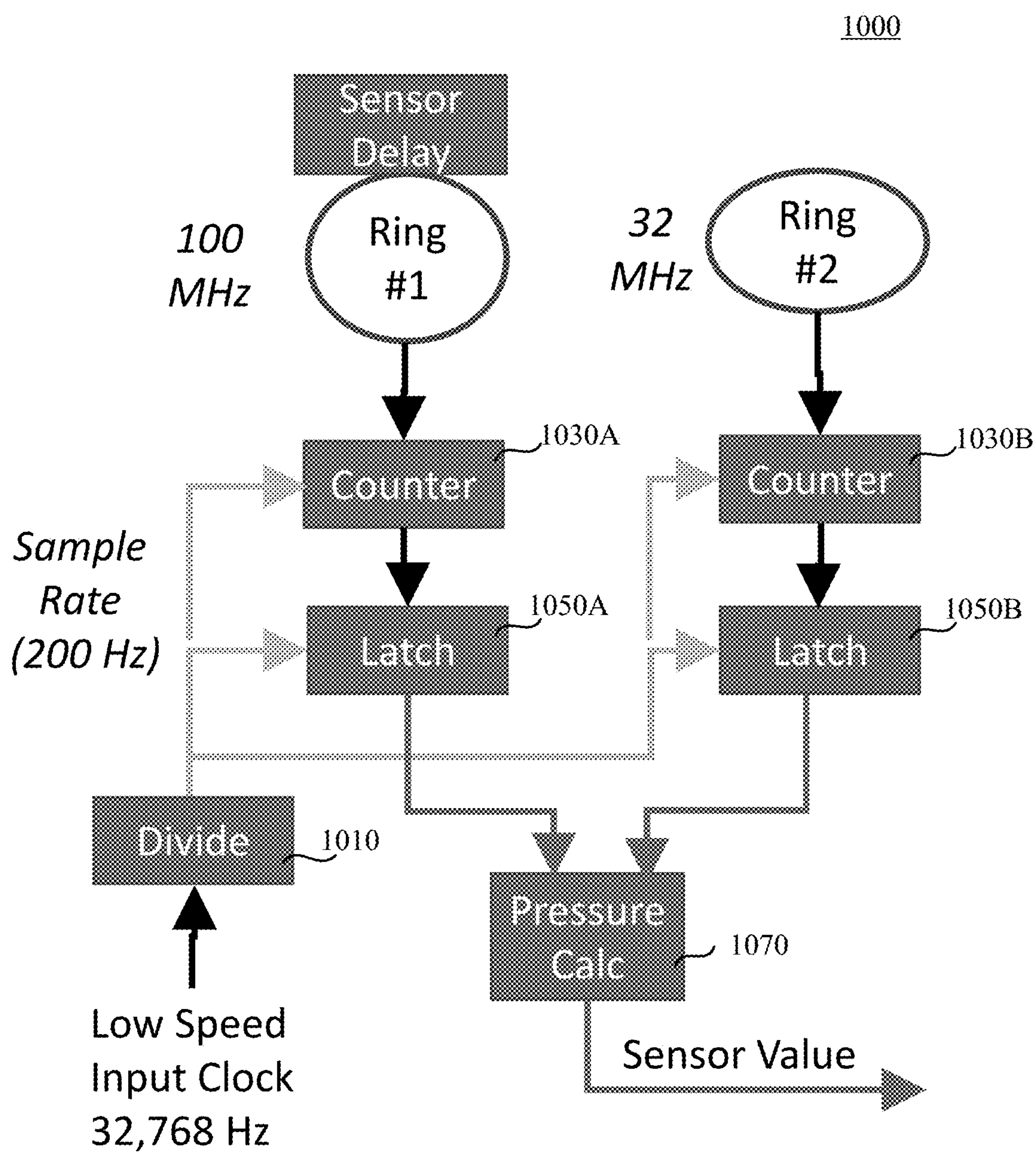
FIG. 10 shows a schematic diagram of a circuit that incorporates two ring oscillator circuits.

FIG. 10 shows a schematic diagram of a sensor 1000 comprising two ring oscillator circuits (e.g., oscillator circuits 900A and 900B) that utilizes a comparison of counts to determine a parameter of interest. Output of the sensor 1000 may be a digital signal, and an ADC does not need to be included in the sensor 1000 (which can save space and/or decrease size). In some variations, the sensor 1000 may be on a single chip. The sensor 1000 may include a first ring circuit (i.e., Ring #1 in FIG. 10) (similar to the first ring circuit described with respect to FIG. 9A) oscillating at a first rate (e.g., 100 MHz), and a second ring circuit (i.e., Ring #2 in FIG. 10) (similar to the second ring circuit described with respect to FIG. 9B) oscillating at a second rate (e.g., 32 MHz). The second rate may vary depending on a first set of parameters (e.g., temperature and voltage) but not a parameter(s) of interest (e.g., pressure), and the first rate may vary depending on the first set of parameters and the parameter(s) of interest. Said similarly, the second rate may vary depending on a set of parameters, and the first rate may vary depending on a different set of parameters. As mentioned above, Ring #1 and Ring #2 may be on the same die. Thus, at least some physical parameters (e.g., the first set of parameters) for both rings will have substantially (e.g., within 1%, within 2%, within 5%, within 10%, within 25%) the same variation (e.g., same silicon process variation, same voltage variation, same temperature variation, etc.). In some variations, Ring #1 and #2 may be on different dies.

Figure 11A:
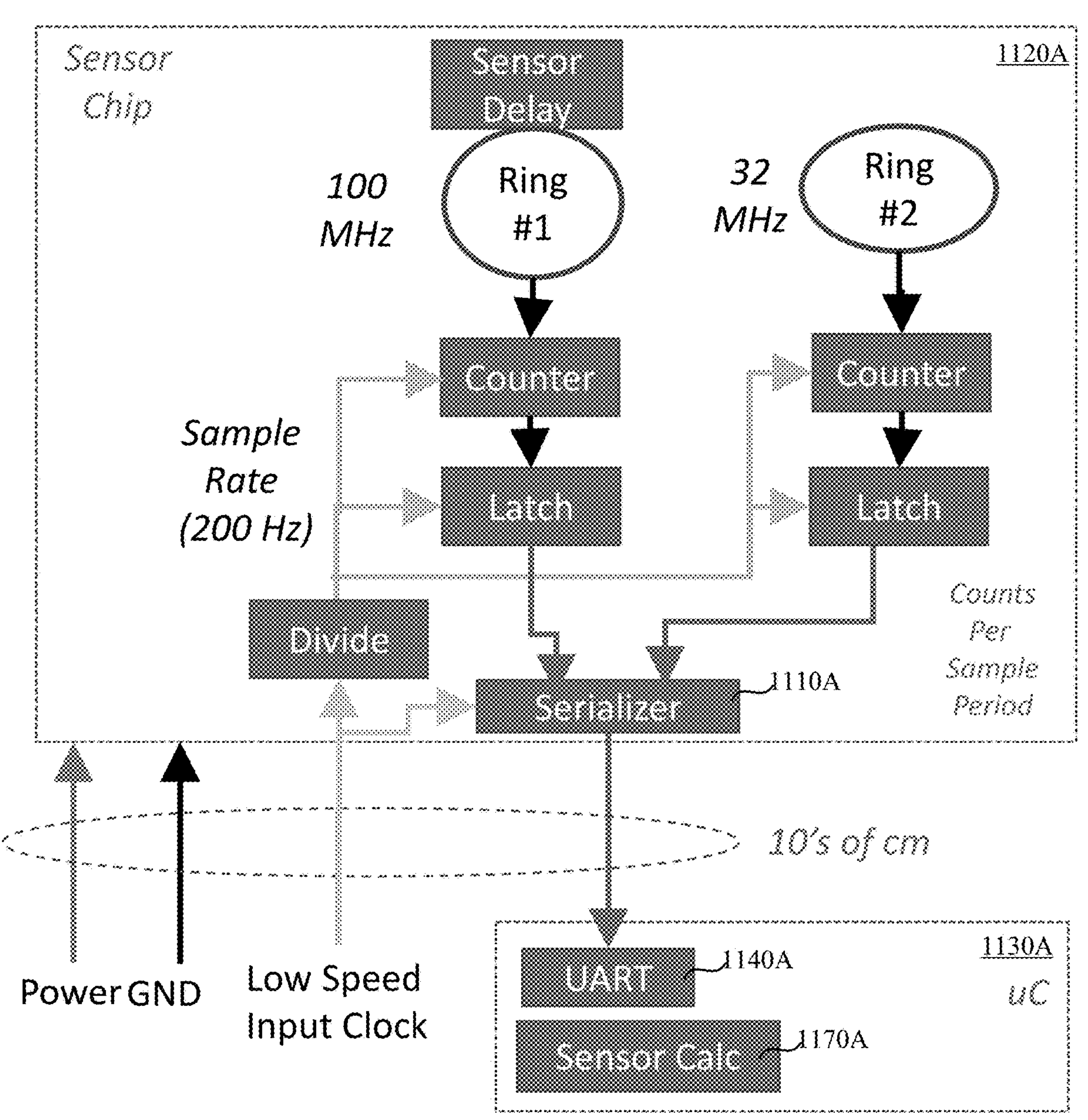
FIGS. 11A and 11B show schematic diagrams of circuits including sensor chips and microcontroller chips.
Figure 11B:
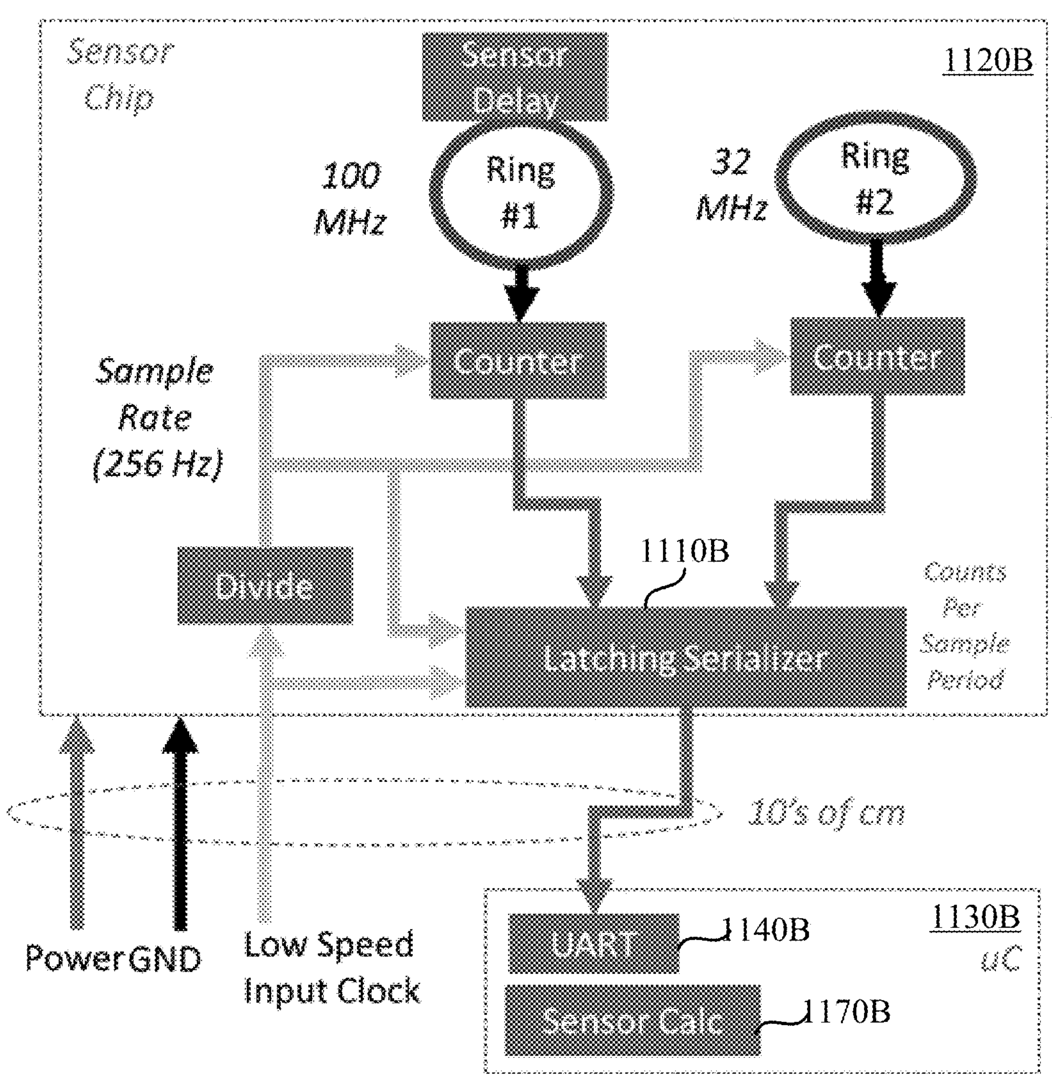

Still referring to FIG. 10, an input clock signal (e.g., 32,768 Hz input clock; i.e., input clock) may be input into a dividing circuit 1010, where the dividing circuit 1010 may output a signal having a predetermined sample rate (e.g., 200 Hz, 256 Hz, etc.). The signal with the predetermined sample rate may then be input into a first rate counter circuit 1030A, a first latch circuit 1050A, a second rate counter circuit 1030B, and a second latch circuit 1050B. For each sample period, the first rate counter circuit 1030A may count the number of oscillations at Ring #1 during that sample period, and the second rate counter circuit 1030B may count the number of oscillations at Ring #2 during that sample period. The first latch circuit 1050A may store a first count value from the first rate counter circuit 1030A at each sample period, and the second latch circuit 1050B may store a second count value from the second rate counter circuit 1030B at each sample period. For each sample period, a parameter of interest calculator circuit 1070 (e.g., third circuit) may receive (1) the first count value (counted by the first rate counter circuit 1030A) from the first latch circuit 1050A at that sample period, and (2) the second count value (counted by the second rate counter circuit 1030B) from the second latch circuit 1050B at that sample period. The parameter of interest calculator circuit 1070 may then use both the first and second count values to determine a value of the parameter(s) of interest (e.g., a pressure value) (e.g., represented as a third signal). In some variations, the parameter of interest calculator circuit 1070 may use one or more look up tables to determine the value(s) of the parameter(s) of interest. In some variations, the parameter of interest calculator circuit 1070 may use an equation that is a function of both the first and second count values to determine the value(s) of the parameter(s) of interest. In some variations, functionalities of the parameter of interest calculator circuit 1070 may be performed on a separate chip, as shown in FIG. 11A or 11B. In some variations, the first count value may be modified based on the second count value to determine the value(s) of the parameter(s) of interest.

Although FIG. 10 shows two ring oscillator circuits (i.e., Ring #1 and Ring #2), in some variations, more than two ring oscillator circuits may be used. In some variations, one or more additional (e.g., a third ring oscillator circuit, a fourth ring oscillator circuit, etc.) may be added to the sensor 1000 shown in FIG. 10. For example, in some variations, a plurality (e.g., two, three, four, or more) of ring oscillator circuits similar to Ring #1 may be used to allow for the determination of the value of another parameter of interest in a similar manner as is described above with respect to FIG. 10. Although FIG. 10 shows the first rate counter circuit 1030A, the first latch circuit 1050A, the second rate counter circuit 1030B, and the second latch circuit 1050B, in some variations, any number of rate counter circuits and/or latch circuits may be used (e.g., one, three, six, eight, etc.). For example, in some variations, the sensor 1000 may further comprise a third ring oscillator circuit that may include a parameter-based delay element that varies delay at a rate different than, for example, other elements in the first, second, and/or third ring oscillator circuits. A difference in count values between the additional (e.g., third, fourth, etc.) ring oscillator circuit and the first and/or second ring oscillator circuits may be used to determine the value of another parameter(s) of interest (e.g., force, light amplitude, audio amplitude, radiation, resistance or capacitance corresponding to a chemical or physical reaction, etc.) In some variations, a difference in count values between an additional (e.g., third) ring oscillator circuit and the first and/or second ring oscillator circuits may be used to measure or otherwise determine die temperature.

In some variations, a temperature of the first or second ring oscillator may be determined using pulse time delay measurements. For example, time for a pulse or a known voltage may be measured, and if the voltage is tightly controlled, an assumption may be made that the time will be different for other pulses based only on temperature.

The various circuits discussed herein may be included on any number of chips, die, and/or substrates. In some variations, the various circuits discussed herein may be included across a plurality of chips, die, and/or substrates. FIG. 11A shows a schematic diagram of a sensor 1100A including a sensor chip 1120A and a compute device, which in this example is a microcontroller chip 1130A. Output of the sensor 1100A may be a digital signal, and an ADC does not need to be included in the sensor 1100 (which can save space and/or decrease size). Circuitry of the sensor chip 1120A may be similar to sensor 1000 of FIG. 10, but may include a serializer circuit 1110A in place of the parameter of interest calculator circuit 1070 from FIG. 10 (which may decrease a size of the sensor chip 1120A). For each sample, the serializer circuit 1110A may receive a first count value of Ring #1 from a first latch circuit and second count value of Ring #2 from the second latch circuit, and provide a serialized representation of both count values to an output circuit 1140A. The serializer circuit 1110A may be electrically coupled to the output circuit 1140A via a wire(s) (e.g., at least 10 cm long, at least 20 cm long, at least 30 cm long, at least 40 cm long, at least 50 cm long, at least 100 cm long, between about 50 and 100 cm). In some variations, the output circuit 1140A is a universal asynchronous receiver-transmitter (UART). Output from the output circuit 1140A may be provided to a parameter of interest calculator circuit 1170A, which may use the output signal from the serializer circuit 1110A to determine a value of the parameter of interest. In some variations, the sensor chip 1120A may include an input/output (I/O) for power, ground, and a clock. In some variations, power may be extracted from the clock to power the sensor chip 1120A. In some variations, the sample rate may be 256 Hz, and the serializer 1110A may output any suitable number of bits each sample period, such as, for example 38 bits or 40 bits each sample period. In some variations, Ring #1 may include one or more inverters (e.g., two, three, or more) and a resistor capacitor (RC) circuit, where a piezoresistive element varies the resistor in the RC circuit. The piezoresistive element may have a resistance between 1999.88 and 2000.12 ohms per mmHg and 5 pF capacitor with delay resulting in the first rate being 90-100 MHz. In some variations, a rolling average (e.g., one second rolling average) of the count values from Ring #2 may be used by the parameter of interest calculator circuit 1170A (e.g., instead of the count values from a single sample period). In some variations, the sensor chip 1120A may communicate with the microcontroller chip 1130A wirelessly. In some variations, the sensor chip 1120A may communicate with the microcontroller chip 1130A via a wired connection (and not wirelessly). In some variations, a sensor includes a first circuit (e.g., oscillator circuit 900A) configured to receive an input clock signal and output a first output count signal at a predetermined sample rate (e.g., 200 Hz, 250 Hz, etc.). The sensor may further include a second circuit (e.g., oscillator circuit 900B) configured to receive the input clock signal and output a second count signal at the predetermined sample rate. The sensor may further include a third circuit (e.g., parameter of interest calculator circuit 1070, sensor chip 1120A, microcontroller chip 1130A, output circuit 1140A, parameter of interest calculator 1170A) coupled to the first circuit and the second circuit. The third circuit may configured to generate a third signal based the first output count signal and the second output count signal (e.g., representing value of a parameter of interest).

FIGS. 11A and 11B show exemplary circuit diagrams for measuring a parameter using two oscillator rings. As shown in FIGS. 11A and 11B, Ring #1 is set to oscillate at a relatively high frequency, and may be in the range of, for example, about 50 MHz to about 100 MHz. The rate at which Ring #1 oscillates may be influenced by several factors, such as, for example, the temperature of the die, the supplied voltage, and the inherent speed of the silicon, which may vary by, for example, +/−20% between different silicon die from different wafers.

The sensor delay may vary according to an attribute that is to be measured. In an example configuration where the sensor delay varies according to pressure, pressure could also affect the speed of the oscillation of Ring #1 by inclusion of a piezo-resistive pressure sensitive unit within the die. Thereby, changes in pressure result directly in changes in the oscillation rate of just Ring #1. Note that oscillating Ring #2 is configured to have no change with respect to the change in pressure (since there is no sensor delay component).

A precise low-speed input clock, such as 32.768 kHz, may be divided to create a sampling rate, such as 200 Hz (e.g., as shown in FIG. 11A) or 256 Hz (e.g., as shown in FIG. 11B). The oscillation of the ring may increment a counter, and at the sampling rate the count value may be latched and the counter may be reset to 0. Thus, at the end of each sample period, the latch may contain the number of oscillations of the ring during the last sample period. For example, for a 256 Hz sample rate, the ring may oscillate many hundreds of thousands of times. For measuring blood pressure in a range of −50 mmHg to +300 mmHg, only 1400 quantizing levels may be needed (e.g., required) to achieve 0.25 mmHg resolution. The 1400 quantizing levels are a small fraction of the 400,000 clocks typically counted during the sample period, and the resolution of the sensor only needs to result in a change in a few counts of the counter. Note that for a 100 MHz oscillation rate, 1 count is only 10 nanoseconds. So a change in pressure of 1 mmHg only needs to result in a 50-100 nanosecond change in the delay time.

Ring #2 in FIGS. 11A and 11B may be configured to be latched at the same rate as Ring #1, but because Ring #2 doesn't have the piezo-resistive element (i.e., sensor delay) as part of its structure, Ring #2's oscillation rate may be insensitive or agnostic to the change in the pressure. Thus the oscillation rate of Ring #2 may be influenced only by, for example, the temperature, voltage and inherent properties of the silicon. As the temperature of the die increases, the oscillation rate will slow down, and as the temperature decreases, the oscillation rate will speed up. Similarly, as the voltage increases, the oscillation rate will increase and as the voltage decreases the oscillation rate will decrease. Because Ring #2 is on the same silicon die as Ring #1, the temperature and voltage may be the same, and the variations due to temperature and voltage may be identical to that of Ring #1. The changes in the latched values for Ring #2 may then be used when calculating the sensed property measured by Ring #1. As such, Ring #2 may act like a continuous calibration of the sensor die, with a recalibration performed at the sample rate.

In variations in which the sensors described herein are utilized to measure pressure in a clinical setting, a system or medical device with a pressure sensor may be "tared" (zeroed) prior to insertion into the body. The system or device may then be configured to determine and/or store the clock rate for both rings. When the sensor is placed within the body, the temperature may go up, and Ring #2 may run slower. The amount Ring #2 runs slower may be factored into the calculations for converting the Ring #1 rate to pressure.

While any clock may be used for the low-speed input clock, in some variations, a 32.768 kHz clock maybe desirable. For example, in variations in which preciseness is particularly desirable because, the sensors described herein may utilize clocks that are derived from crystals. These crystals routinely achieve accuracies of +/−5 ppm (0.0005%), thus use of these crystals would add only a small error (which is likely to be essentially inconsequential (estimated to be in the range of mmHg for a pressure sensor)).

Once the two counter values are latched, a small area on the die may be used to send those values out as a digital output (e.g., digital communications packet). In some variations, the values may be transmitted as a serial packet that maybe read directly by a compute device (e.g., microcontroller 1130A or 1130B). In some variations, the Universal Asynchronous Receiver Transmitter (UART) protocol h may be utilized. The UART protocol supports communications packets that may be as short as 1 byte and as many as thousands of bytes. As an example, in a variation in which each counter is 19 bits, only 38 bits need to be sent, which may fit within a simple 5 byte (40 bit) packet. While UART is discussed herein and may in some variations be utilized, in other variations, other communication protocols may be used instead of or in addition to UART.

At least some variations described herein may use two or more rings, and the use of a compute device to perform the run-time calibration.

While the above example involves pressure measurement, the same general technique may measure other physical properties such as force, light amplitude, acoustics, or electrochemical reactions. The sensor delay may result in a measurable change in an impedance, capacitance, or inductance; otherwise, the sensor delay could result in a change in the propagation speed of the electrical signals within the ring.

One benefit of this sensor arrangement is that the die is not limited to 2 rings. For example, in some variations, the sensors described herein may comprise a 3rd ring with an oscillation rate that may be modified by a different physical property. For example, the 3rd ring may be set up to have additional sensitivity to temperature (vs. Ring #2) and thus may provide a highly accurate report of a patient's core temperature. A 4th ring may be employed with an oscillation rate that may vary based on electrochemical properties, such as pH. At higher sample rates, it may be possible to pick up acoustic signatures associated with heart valve opening/closing. In each of these variations, the analog signals may be converted to digital data that may be sent via a single wire using digital messages. Additional sensing may simply require a slightly larger message. For example, at a 256 Hz sample rate and a 32.768 kHz input clock, a single output wire may send out 128 bits during each sample period. This could accommodate 5 different sensors, each with 19 bit resolution. If more resolution or a higher sample rate is desired, the clock rate may be doubled or one or more additional wires may be added. The ability to transition from analog to digital signaling has tremendous implications for signal fidelity, interoperability with existing patient monitoring devices, and miniaturization of SSPT devices, and may be applied across many aspects of patient care, especially in prolonged field care (PFC) where size and power requirements are paramount.

As can be seen, FIG. 11B shows a sensor chip 1120B and a microcontroller chip 1130B. Sensor 1110B is substantially similar to sensor 1110A from FIG. 11A, but has a different sample rate; sensor 1100B uses a 256 Hz sample rate, while sensor 1100A uses a 200 Hz sample rate. Although FIG. 11A shows the serializer 1110A as separate from the two latches, latching serializer 1110B from FIG. 11B may be a combination of the two latches and serializer 1110A from FIG. 11A. Of course, 200 Hz and 256 Hz sample rates are examples, and some variations may use different sample rates.

Figures 13A, 13B:
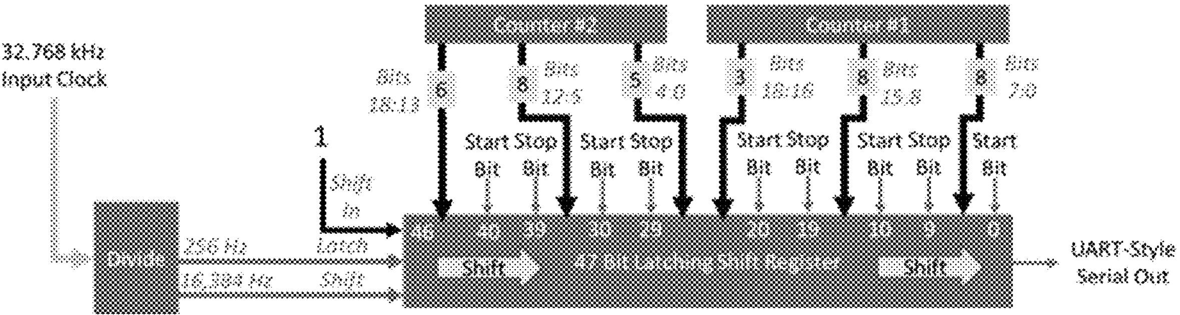
FIGS. 13A and 13B show an example of a latching serializer communicatively coupled to multiple counters, and an example of a UART output from the latching serializer, respectively.

In some variations, start and stop bits may be latched directly into the shift register. For example, FIG. 13A shows an example of a latching serializer communicatively coupled to two 19-bit counters (e.g., similar to the latching serializer 1110B in FIG. 11B, similar to serializer 1110A and the two latches coupled to serializer 1110A in FIG. 11A, etc.). In the example shown at FIG. 13A, a 32.768 kHz input clock is divided into a 256 Hz latch signal and a 16,384 Hz shift signal. A 47 bit latching shift register receives a 1 shift in signal, the latch signal, and the shift signal, as well as values from each of the two 19 bit counters, start bits, and stop bits. In this variation, the 47 bit latching shift register outputs a UART-style serial output. Based on the 256 Hz latch signal, the counter values and the UART start bits ("0") and stop bits ("1") are latched in right order directly into the 47-bit output shift register. The shift register "shifts" based on the 16,384 Hz clock. This will result in 64 bits during each of the 1/256 Hz sample periods (16,384 bits/256=64). After sending out the first 47 bits, because a "1" is shifted in, the next 17 bits sent will all be 1. These "1's" properly complete byte 5 (including its stop bit) and result in 14 idle ("1") bits before the next frame. The UART-style serial output is shown in FIG. 13B. Each frame has a certain number of bytes within no delay between each byte. During idle time between frames, in some variations, the digital output may be high (represented by 1). In some variations, each data byte is preceded by a single start bit (e.g., low) and a single stop bit (e.g., high). In some variations, the individual data bits within a byte are sent most significant bit first. In one example, the 5 bytes within a frame may be: (1) Byte 1: Bit 7=Ring #1 count bit 18; Bit 6=Ring #1 count bit 17; . . . ; Bit 0=Ring #1 count bit 11; (2) Byte 2: Bit 7=Ring #1 count bit 10; Bit 6=Ring #1 count bit 9; . . . ; Bit 0=Ring #1 count bit 3; (3) Byte 3: Bit 7=Ring #1 count bit 2; Bit 6=Ring #1 count bit 1; Bit 5=Ring #1 count bit 0; Bit 4=Ring #2 count bit 18; Bit 3=Ring #2 count bit 17; . . . ; Bit 0=Ring #2 count bit 14; (4) Byte 4: Bit 7=Ring #2 count bit 13; Bit 6=Ring #2 count bit 12; . . . ; Bit 0=Ring #2 count bit 6; (5) Byte 5: Bit 7=Ring #2 count bit 5; Bit 6=Ring #2 count bit 4; . . . ; Bit 2=Ring #2 count bit 0; Bit 1=Always 1; Bit 0=Always 1. One benefit of the variations shown at FIGS. 13 and 13B is that state machines (e.g., to keep track of byte or packet boundaries) are not needed.

In one example, the serial output may be at a rate that is half the input clock. In one example, a single flip flop may be used to create a 16,384 kHz clock, and a 6 flip flop divider of that 16,384 kHz clock is used to get a 256 Hz sample rate. At each sample boundary, the values from the two counters may be latched. In some variations, rather than build state machines to handle the start/stop bits, the 38 counter bits (2×19) and the start/stop bits may be latched directly into a single 47 bit shift register. In one example, the shift register only needs to be 47 bits (and not 50 bits) because there are 10 bits per byte, but the last 3 bits of byte 5 are always 1. At the output clock rate (16,384 kHz), a bit from the shift register is shifted out and a "1" is shifted in at the other end. This will enforce the "1" as the output during the time between the 5 bytes b. Output Device Generally, an output device as described herein may be configured to output a signal corresponding to a measured parameter as described herein. For example, the output signal may be a digital signal such that circuits such as an ADC are not needed, thus reducing device complexity. In some variations, a controller 320 may comprise an output device 328 configured to output the third signal 532 as a digital signal. For example, the output device 328 may be configured to output the third signal 532 as a set of binary encoded bits at a periodic rate. In some variations, the output device 328 may comprise one or more of a wire configured for wired transmission and an antenna configured for wireless transmission. In some variations, the third signal 532 may be encoded and/or output on a separate wire to increase noise immunity.

As described herein, a measured parameter may be represented by 4,096 quantized levels that may be transmitted as a digital signal using 12 bits at a predetermined rate (e.g., once per 5 milliseconds, 3,200 bits per second). It should be appreciated that transmission speeds below 5,000 bits per second have high noise reliability because each bit is long enough that the noise bursts are shorter than the individual bit time.

In some variations, the digital signal comprises one or more of standard binary encoding (e.g., UART), Pulse Width Modulation (PWM), Manchester encoding, and the like. In some variations, the output device may comprise a universal asynchronous receiver-transmitter (UART). Accordingly, the output device may be absent a PGA and/or ADC, thus reducing component count and manufacturing complexity. In some variations, the digital signal may be output using one or more of a wire and antenna. There are several methods for providing the binary encoded value on a single wire including a standard NRZ or NRZI UART technique, with a start bit, 8 encoded bits, and a stop bit. In some variations, the digital signal may be output as multiple bytes of ASCII text and/or greyscale encoding.

In some variations, the output device may include a serializer (e.g., serializer circuit 1120), where the serializer may include circuitry configured to convert parallel data to serial data and/or vice versa. In some variations, the output device may include an output register, where the output register may include circuitry that includes flip flops and is configured to store data.

c. Processor

A sensor system 300, as depicted in FIG. 3, may comprise a processor 322 and a machine-readable memory 324 (e.g., collectively a controller) in communication with one or more compute devices 340. The processor 322 may be connected to the compute devices 340 by wired or wireless communication channels. The processor 322 may be configured to control one or more components of the sensor system 300, such as the communication device 330. The processor 322 may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

The processor 322 may incorporate data received from the memory 324 and compute device(s) 340 to control the system 300. The memory 324 may further store instructions to cause the processor 322 to execute modules, processes, and/or functions associated with the system 300 and/or compute device(s) 340. The processor 322 may be any suitable processing device configured to run and/or execute a set of instructions or code and may comprise one or more microcontrollers, data processors, image processors, graphics processing units, physics processing units, digital signal processors, and/or central processing units. The processor 322 may be, for example, a general purpose processor, a Field Programmable Gate Array (FPGA), an Application Specific Integrated Circuit (ASIC), configured to execute application processes and/or other modules, processes, and/ or functions associated with the system and/or a network associated therewith. For example, the processor 322 may be a dual core microcontroller. The underlying device technologies may be provided in a variety of component types such as metal-oxide semiconductor field-effect transistor (MOSFET) technologies like complementary metal-oxide semiconductor (CMOS), bipolar technologies, polymer technologies (e.g., silicon-conjugated polymer and metal-conjugated polymer-metal structures), mixed analog and digital, combinations thereof, and the like.

d. Memory

Some variations of memory 324 described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as air or a cable). The media and computer code (also may be referred to as code or algorithm) may be those designed and constructed for a specific purpose or purposes. Examples of non-transitory computer-readable media include, but are not limited to, flash memory, non-volatile memory (e.g., Intel® Optane™, 3D XPoint™), magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical discs; solid state storage devices such as a solid state drive (SSD) and a solid state hybrid drive (SSHD); carrier wave signal processing modules; and hardware devices that are specially configured to store and execute program code such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

e. Communication Device

In some variations, sensor systems 300 described herein may communicate with one or more of a blood control device, networks, and computer systems through a communication device 330. In some variations, the sensor systems 300 may be in communication with other devices (e.g., compute devices) via one or more wired and/or wireless networks. A wireless network may refer to any type of digital network that is not connected by cables of any kind. Examples of wireless communication in a wireless network include, but are not limited to Bluetooth, cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system. In some variations, any of the data stored in memory 324 may be transmitted using the communication device 330.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some variations, the network interface may comprise a radiofrequency receiver, transmitter, and/or optical (e.g., infrared) receiver and transmitter. The communication device 330 may communicate by wires and/or wirelessly with one or more components of the systems 300.

II. Sensor Housing

The sensors described herein may be contained in, positioned within, and/or encapsulated in a sensor housing and integrated into an elongate body (e.g., a catheter) used in various devices, such as, for example, blood flow control devices and pressure monitoring devices, as further described below. The sensors may monitor physiologic conditions during a medical procedure and/or monitor patient physiology during routine and critical medical care. In some variations, the sensor housing may be a tubular member including an opening (e.g., a window) configured to expose the sensor to the surrounding environment (e.g., blood within a blood vessel) and/or one or more struts to aid in attaching the sensor housing (and thus the sensor) to the elongate body. In some variations, the sensor housing may be coupled to or otherwise affixed to a sleeve. The sleeve may be positioned around or may otherwise encircle the elongate body, thereby coupling the sensor to the elongate body. One or more sensor housings may be integrated into the elongate body, depending on the number of sensors included in the elongate body. In another variation, the sensor and/or the sensor housing may be configured to be small in size (e.g., have a small diameter) so that the sensor may be integrated into an elongate body (e.g., a catheter) for advancement into a blood vessel or advanced through an arterial or venous catheter (e.g., an arterial or venous access line). The sensor housing may be configured to protect the sensor(s) from damage due to moisture or fluid intrusion (e.g., upon exposure to blood) and/or protect the sensor(s) from the effects of pressurization (e.g., pressure from a balloon of a blood flow control device).

The sensor housing may be formed of any suitable biocompatible material. For example, in some variations, the sensor housing may be formed from a polymer, such as, for example, Polytetrafluoroethylene (PTFE), polyimide, Pebax®, thermoplastic polymers, a combination thereof, and the like. Exemplary thermoplastic polymers may be a polycarbonate, a polycarbonate/acrylonitrile-butadiene-styrene terpolymer blend, etc. In some variations, the sensor housing may be formed from a metal, e.g., stainless steel, a bondable metal alloy, or a combination thereof. In one variation, the sensor housing comprises stainless steel. In variations in which each of the sleeve and the sensor housing comprise a metal (e.g., stainless steel) tube, the tubes may be laser welded together and an opening may be cut through the tubular wall of both the sleeve and the sensor housing to expose or otherwise provide access to the sensor.

In some variations, as mentioned above, the sensor may be entirely or partially encapsulated in the sensor housing. The sensor may be encapsulated using, for example, various polymers. Encapsulating the sensor in the housing may make the sensor reading less variable to bending forces acting on the sensor and/or may help to isolate the sensor from the effects of pressurization when pressurized devices are employed, e.g., to measure, monitor, and/or adjust blood pressure. Entirely or partially encapsulating the sensor within a polymer may also function as a sealant and protect electrical components of the sensor from moisture or fluid intrusion. Thus, encapsulation within a polymer may make the sensor readings more consistent. In some variations, the sensor may be entirely or partially encapsulated within an RTV (room temperature vulcanized) silicone within a metal (e.g., stainless steel) housing.

Exemplary polymers for use in entirely or partially encapsulating the sensor include without limitation, hydrophobic polymers such as RTV silicone, Polytetrafluoroethylene (PTFE), polyimide, and Pebax®, and combinations thereof. In one variation, encapsulating the sensor may include forming a layer of polymer, e.g., a layer comprising an RTV silicone or a different polymer, in the sensor housing, placing the sensor on the polymer layer and then curing the polymer. Next, the sensor may be encapsulated by covering the sensor with additional polymer, e.g., RTV silicone, and then curing the polymer. The polymer may have a compliance that allows transmission of pressure signals through it so that physiologic conditions, such as, for example, pressure, may be transmitted through the polymer to the sensor. In some variations, separate seals (e.g., epoxy seals) may be disposed within the sensor housing to protect the sensor from the effects of pressurization. Instead of encapsulating the sensor, the polymers described herein may also be employed to coat the sensor and any associated component (e.g., wires, wire pads). In variations in which the sensor is not encapsulated, the aforementioned polymers may be used to adhere the sensor to the sensor housing or an adhesive may be used to fix the sensor to the sensor housing.

The sensor housing may have any suitable size, shape, and geometry. For example, the sensor housing may have a tubular, a rectangular, a square, or an ovular shape. In one variation, the sensor housing may be tubular in shape and include an opening (e.g., a window) as mentioned above. The dimensions of the sensor housing may be such that the sensor tightly fits in the sensor housing, thereby minimizing the utilization of space on the elongate body.

A. Tubular Sensor Housing

As mentioned above, in some variations, the sensor housing may comprise a tubular shape. In these variations, the inner diameter of the sensor housing may be about 0.01 inches to about 0.04 inches, including all values and sub-ranges therein. In some variations, the inner diameter of the sensor housing may be for example about 0.012 inches (0.30 mm) to about 0.035 inches (0.89 mm), about 0.015 inches (0.38 mm) to about 0.03 inches (0.76 mm), about 0.017 inches (0.43 mm) to about 0.025 inches (0.64 mm), or about 0.019 inches (0.48 mm) to about 0.022 inches (0.56 mm), including all values and sub-ranges therein. In one variation, the inner diameter of the sensor housing may be about 0.02 inches (0.51 mm). In some variations, the outer diameter of the sensor housing may be about 0.02 inches (0.51 mm) to about 0.08 inches (2.0 mm), including all values and sub-ranges therein. In some variations, the outer diameter of the sensor housing may be for example about 0.021 inches (0.53 mm) to about 0.06 inches (1.5 mm), about 0.022 inches (0.56 mm) to about 0.04 inches (1.0 mm), about 0.023 inches (0.58 mm) to about 0.03 inches (0.76 mm), about 0.024 inches (0.61 mm) to about 0.027 inches (0.69 mm), including all values and sub-ranges therein. In one variation, the outer diameter of the sensor housing may be about 0.025 inches (0.64 mm).

Figure 17A:
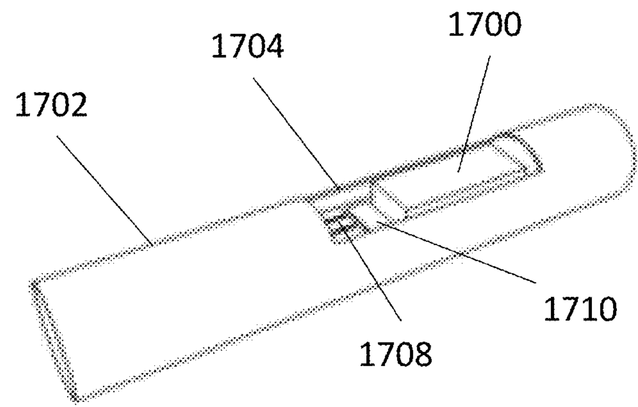
FIGS. 17A-17C show a perspective view, a top view, and a front view of a sensor coupled to an exemplary sensor housing.
Figure 17B:
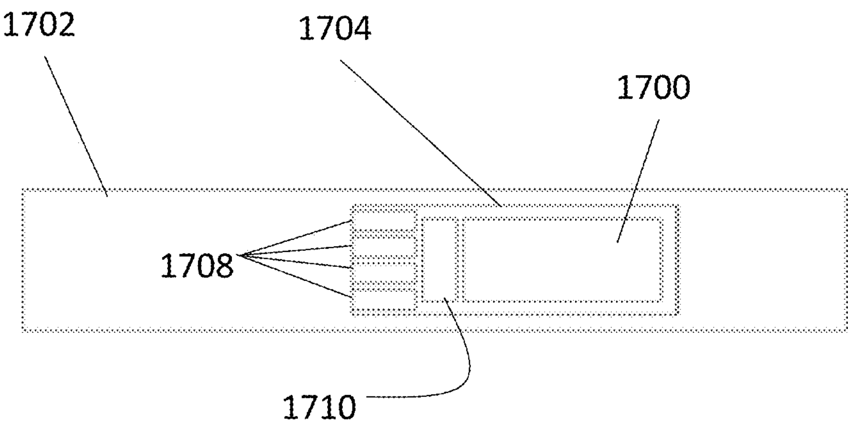
Figure 17C:
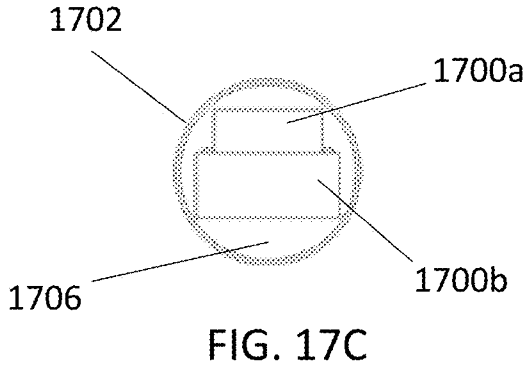

FIGS. 17A-17C show an exemplary tubular sensor housing. Referring to FIGS. 17A-17C, sensor 1700 may be disposed within a tubular sensor housing 1702. The sensor 1700 may include a MEMS piezoresistive sensor **1700*a* on a CMOS bare die 1700*b*. A window 1704 formed through the wall of the tubular sensor housing 1702 may expose the sensor 1700 to the external environment (e.g., blood flowing through an artery or vein). As shown in the cross-sectional view of FIG. 17C, the sensor 1700 may be sized such that the sensor 1700*a* and die 1700*b* fit tightly within the lumen 1706 of the tubular sensor housing 1702. An adhesive, e.g., an RTV adhesive, may be included in the tubular sensor housing 1702 (e.g., below the sensor 1700) to secure the sensor 1700 thereto. In some variations, the adhesive may also be included to partially or entirely encapsulate the sensor 1700 in the tubular sensor housing 1702. Wire bond pads 1708 for connecting the CMOS circuitry 1710 on the sensor 1700 may be fed through the window 1704 and then coated (or encapsulated) with adhesive (e.g., the adhesive used to encapsulate or attach the sensor 1700 to the tubular housing 1702**).

The sensor contained within the tubular sensor housing (e.g., the housing of FIGS. 17A-17C) may have any width and thickness that allows it to be incorporated into a sensor housing and/or an elongate body, and may vary depending on the parameter being measured and/or the device in which it is included (e.g., a blood flow control device, a pressure measurement device, other medical or non-medical devices that measure one or more of temperature, voltage, force, pressure, light amplitude, and audio amplitude). In some variations, the sensor may be configured to have any width, thickness, and height as previously described herein. In other variations, the sensor width may be about 330 microns and the sensor thickness may be about 250 microns.

B. Sensor Housing with Struts

Some variations of the sensor housing may include one or more structural components configured to couple the sensor housing to an elongate body (e.g., a catheter). The structural components may be configured as struts having edges that may be useful in attaching (e.g., welding) the sensor housing to the elongate body. For example, the window of the sensor housing may be aligned with an opening in the elongate body and the struts attached to the elongate body at one or more of the strut edges. The height of the struts may be such that the sensor housing is appropriately positioned within the lumen of the elongate body and relative to the elongate body to minimize interference with external elements that may affect sensor functionality. For example, the sensor may be exposed just enough to acquire accurate sensor measurement, but may be protected from damage by its placement within the sensor housing.

Figure 18:
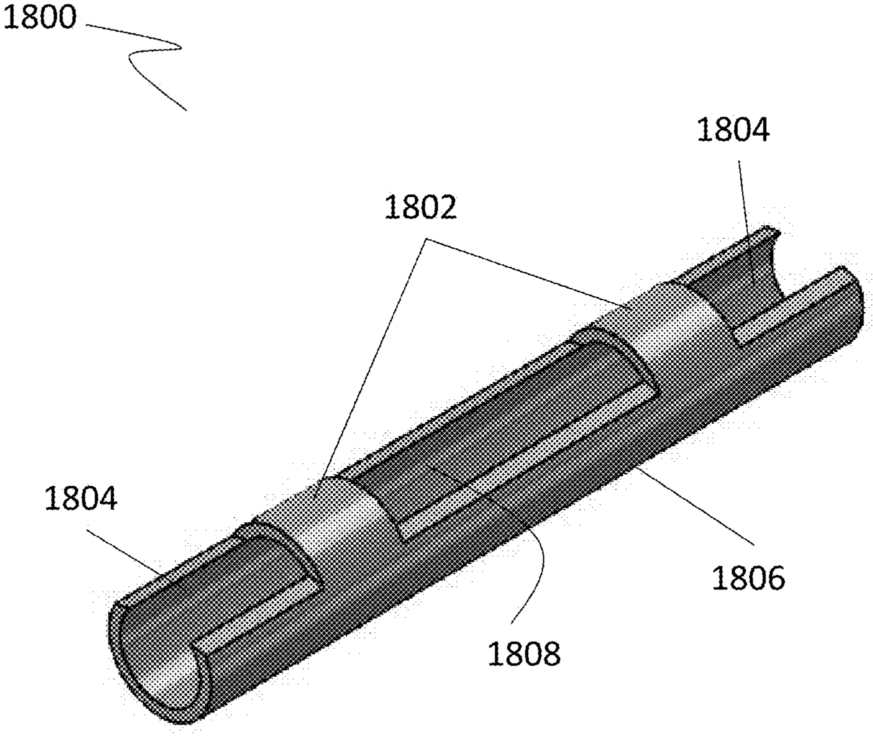
FIG. 18 shows an exemplary sensor housing including struts and cutouts to aid with attaching a sensor to an elongate body and/or a sensor sleeve.

For example, as shown in FIG. 18, the sensor housing 1800 may include a body portion 1806, a window 1808, cutouts 1804, and two struts 1802 that may be used to couple the sensor housing 1800 to an elongate body (e.g., not shown). The struts 1802 and cutouts 1804 to the outside of the struts 1802 may help to attach (e.g., laser weld) the sensor housing 1800 to the elongate body. The sensor housing 1800 may have a diameter sized to fit within the elongate body, and in some variations may have a diameter of about 0.1 Fr to about 5 Fr, including all values and sub-ranges therein. For example, the sensor housing may be about 0.1 Fr, about 0.2 Fr, about 0.3 Fr, about 0.4 Fr, about 0.5 Fr, about 0.6 Fr, about 0.7 Fr, about 0.8 Fr, about 0.90 Fr, about 1 Fr, about 2 Fr, about 3 Fr, about 4 Fr, or about 5 Fr. Sensor housings having a size of about 1 Fr may be useful for medical applications, e.g., when the sensors are threaded through previously placed arterial or venous catheters.

C. Sensor Sleeve

In some variations, a sleeve may be used to assist in coupling a sensor housing to an elongate body (e.g., a catheter) of device (e.g., a blood flow control device). In these variations, the sensor housing may be coupled to or otherwise affixed to the sleeve, which may be positioned around to partially or fully encircle the elongate body, thereby coupling the sensor to the elongate body, as previously described.

The sleeve may be configured to receive the elongate body thereby coupling or integrating the sensor housing, and thus the sensor, to or with the elongate body. The sleeve may include a lumen configured to receive the elongate body, an opening (e.g., a window) such that the sensor housing may be exposed therethrough, and in some variations, a feature to facilitate progressive transition of stiffness between the elongate body and the sleeve.

In some variations, the sleeve may be sized and shaped such that the elongate body may be received within the sleeve. For example, the sleeve may comprise a lumen therethrough with a cross-sectional shape corresponding to a cross-sectional shape of the elongate body and with a diameter larger than an outer diameter of the elongate body. For example, in some variations, the sleeve may be tubular. In some variations, the sleeve may add stiffness to the elongate body around the sensor contained within the sleeve, thereby protecting the sensor from damage and isolating the sensor from sensitivity related errors that may occur due to flexing of the elongate body.

The sleeve may be made from any suitable biocompatible material. For example, the sleeve may be formed from a polymer, such as, for example, Polytetrafluoroethylene (PTFE), polyimide, Pebax®, thermoplastic polymers, a combination thereof, and the like. Exemplary thermoplastic polymers may be a polycarbonate, a polycarbonate/acrylonitrile-butadiene-styrene terpolymer blend, and the like. In some variations, the sleeve may be formed from a metal, e.g., stainless steel, a bondable metal alloy, or a combination thereof. In one variation, the sleeve comprises stainless steel.

In some variations, the sleeve may include a feature that may enable progressive transition of stiffness of the elongate body and may distribute unwanted external forces (e.g., bending forces) acting on the elongate body. For example, in some variations, the sleeve may be stiffer than the elongate body and/or the combination of the elongate body and the sleeve together may make the portion of the device with the sleeve stiffer than the portions of the elongate body without the sleeve. In these variations, the sleeve may include slits and/or openings to ease the transition between the portions of the device with and without the sleeve. The slits or openings may be formed in any suitable shape or pattern, such as, for example, in a spiral shape. In some variations, the slits and/or openings may only be positioned in a transition zone on the sleeve (e.g., on one or both ends of the sleeve), while in other variations the slits and/or openings may be along the entire length of the sleeve. The transition zone may facilitate progressive transition from a less stiff elongate body segment to the more stiff sleeve portion. This may especially provide the benefit of distributing bending forces when the elongate body is flexing.

The sleeve may comprise one or more sleeve openings, which may, in some variations, receive at least a portion of the sensor housing and/or sensor therein and may expose a portion of the sensor housing and thus at least a portion of the sensor positioned therein. A portion of the sensor and/or a portion of the sensor housing may be aligned with the sleeve opening to expose the sensor. For example, a portion of the sensor and/or a portion of the sensor housing may be aligned with the sleeve opening along a depth of the sleeve. For instance, the portion of the sensor and/or the portion of the sensor housing may be positioned underneath the sleeve opening and may be aligned with the opening axially. In some variations, a portion (e.g., a structural component) of the sensor housing may traverse the sleeve opening and may be utilized to secure the sensor housing to the sleeve.

The sensor housing and/or the sensor may be inserted into and/or positioned within the sleeve such that the sensor housing sits within the lumen of the sleeve. Thus, the sleeve and the sensor housing may be configured such that at least a portion of the sensor housing and/or the sensor (e.g., surface of the sensor) may be aligned with an outer surface of the elongate body. Put another way, the sensor housing and/or the sensor may be inset in the sleeve at a depth selected to allow the sensor housing and/or the sensor to be aligned with an outer surface or sidewall of the elongate body. The sensor housing and/or the sensor may be aligned with an outer surface or sidewall of the elongate body such that they are flush. The sleeve opening may allow the sensor to be exposed to the conditions in a patient's body in order to obtain measurements, while the sensor remains protected within the sensor housing. In some variations, the elongate body may include an elongate body opening, window and/or cavity to receive the sensor housing.

In some variations, instead of a window, the sleeve may comprise one or more sleeve recessed portions configured to receive at least a portion of the sensor housing therein. When the sleeve is coupled to the elongate body, the sleeve recessed portion may be aligned with the opening and/or window of the elongate body. The sensor housing may be inserted into and/or positioned within the sleeve recessed portion, which may then be received within the opening and/or window of the elongate body. In this way, the sensor housing may be received within the opening and/or window on the elongate body such that it is aligned with an outer surface or sidewall of the elongate body. In some variations, the sensor may not be contained within or encapsulated in a sensor housing. Rather, the sensor may be inserted into and/or positioned within the sleeve such that the sensor sits within the lumen of the sleeve and at least a portion of the sensor may be aligned with an outer surface of the elongate body. In such variations, adhesive may be applied along a perimeter of the sensor to additionally secure the sensor to the sleeve. For example, the sleeve may further comprise one or more holes to provide access point(s) for applying the adhesive to secure the sensor to the sleeve. In some variations, the one or more holes in the sleeve may be used to provide access point(s) for introduction of an adhesive in an amount that wholly or partially encapsulates the sensor in the sensor housing.

Figure 19:
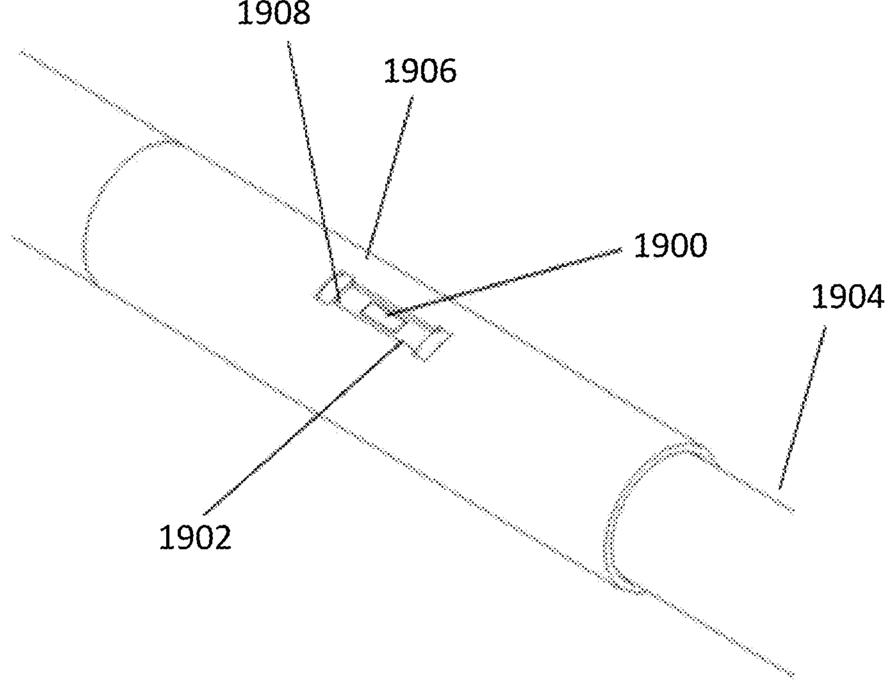
FIG. 19 shows an exemplary variation of a sensor coupled to an elongate body using a sensor sleeve.

FIG. 19 depicts an exemplary variation of a sensor 1900 and sensor housing 1902 attached to an elongate body 1904 via a sensor sleeve 1906. Referring to FIG. 19, the sleeve 1906 may include a sleeve opening 1908 to receive a portion of the sensor housing 1902 therein and to expose a portion of the sensor 1900 contained in the sensor housing 1902. A portion of the sensor housing 1902 may be inserted into and/or positioned within the sleeve opening 1908 and the remainder of the sensor housing 1902 may sit within the lumen (not shown in FIG. 19) of the sleeve 1906. In this manner, the sensor housing 1902 and/or a sensing surface of the sensor 1900 may be aligned with an outer surface or sidewall of the elongate body 1904. As previously described herein, the sensor 1900 may be encapsulated (e.g., entirely contained within a polymer) or otherwise sealed within the sensor housing 1902 using a polymer (e.g., an RTV silicone) to make the sensor readings less variable to bending forces acting on the sensor and/or to protect electrical components of the sensor from moisture, fluid intrusion, etc. In some instances, a hydrophobic polymer coating (e.g., a parylene coating) may be applied to protect against moisture and/or fluid intrusion. The physiologic condition the sensor is configured to measure may be transmitted through the polymer to the sensor 1900.

Methods

Also described here are methods for measuring a physical property using the devices and systems described herein. In particular, the systems, devices, and methods described herein may be used to accurately measure a parameter in a fewer number of steps and in a compact circuit configuration form factor. Generally, the methods described here comprise generating a plurality of output clock signals using an input clock signal and an adjustable delay. A difference between the output clock signals corresponds to a measurement parameter.

Figure 6:
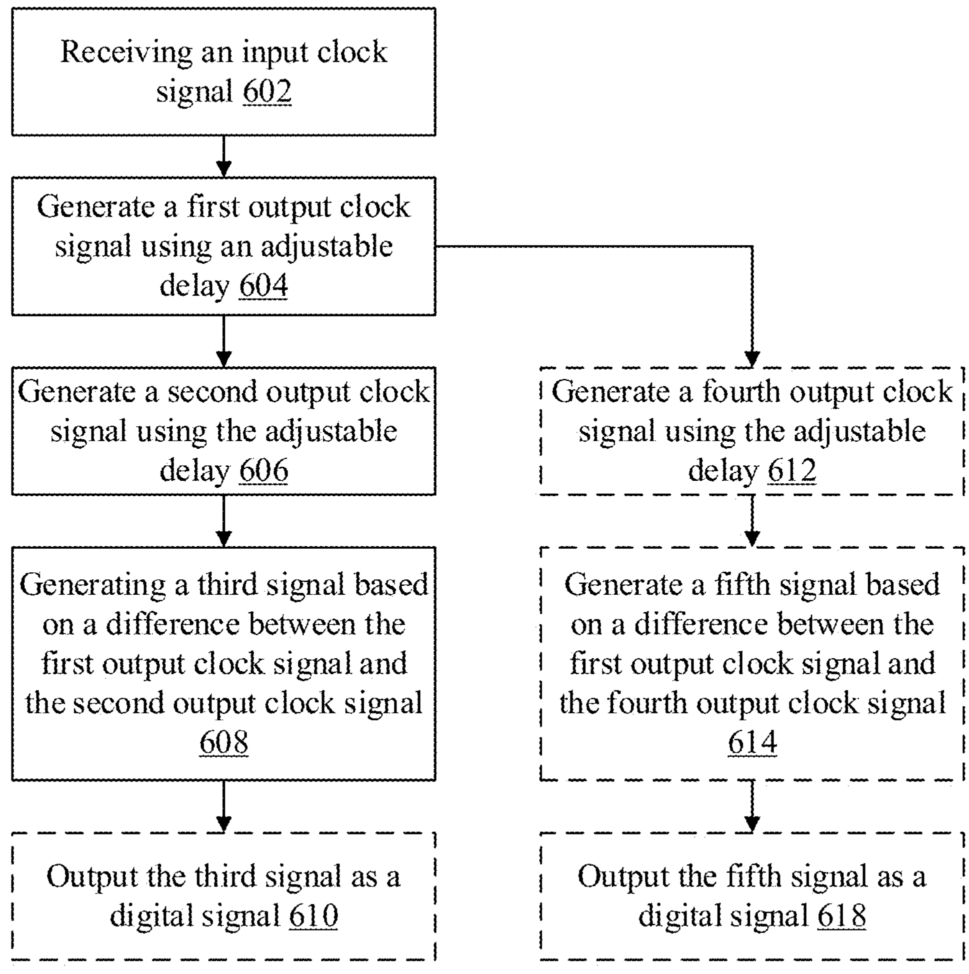
FIG. 6 depicts a flowchart representation of an illustrative variation of a method of measuring a parameter.

FIG. 6 depicts a flowchart describing a variation of a method 600 of measuring a parameter. In the variation depicted in FIG. 6, the method 600 of measuring a parameter may comprise receiving an input clock signal in step 602.

In step 604, a first output clock signal may be generated having a predetermined ratio between the input clock signal and the first output clock signal using an adjustable delay. In some variations, a frequency of the first output clock signal may be greater than a frequency of the input clock signal.

In step 606, a second output clock signal may be generated using the adjustable delay. In some variations, a frequency of the second output clock signal may be greater than a frequency of the input clock signal.

In some variations, the first output clock signal may vary based on a first set of parameters and the second output clock signal may vary based on a second set of parameters different from the first set of parameters. For example, the second set of parameters may include first set of parameters and at least one additional parameter (e.g., the parameter of interest to be measured). In some variations, the first set of parameters may comprise one or more of temperature and voltage. For example, the second set of parameters may comprise temperature, voltage, and one or more of force, pressure, light amplitude, audio amplitude, and resistance or capacitance corresponding to a chemical or physical reaction.

In step 608, a third signal may be generated based on a difference between the first output clock signal and the second output clock signal. In some variations, the third signal may correspond to one or more of temperature, voltage, force, pressure, light amplitude, and audio amplitude.

Optionally, in step 610, the third signal may be output as a digital signal. For example, the third signal may be output as a set of binary encoded bits at a periodic rate.

Optionally, in step 612, the method may comprise generating a fourth output clock signal using the adjustable delay and optionally, in step 614, may further comprise generating a fifth signal based on a difference between the first output clock signal and the fourth output clock signal. In some variations, the fifth signal may correspond to one or more of temperature, voltage, force, pressure, light amplitude, and audio amplitude.

Optionally, in step 618, the method may further comprise outputting the fifth signal as a digital signal. For example, the fifth signal may be output as a set of binary encoded bits at a periodic rate.

FIG. 12 depicts a flowchart of an illustrative method 1200 of determining a value associated with a physical parameter of interest at a sensor. In step 1202, a first count number indicating a number of oscillations at a first ring oscillator circuit during a sample period is obtained. The first ring oscillator circuit may be associated with (e.g., included in) a sensor and may oscillate at a first oscillation rate. The first oscillation rate may be based on a first set of physical parameters and a second physical parameter (i.e., physical parameter of interest). In step 1204, a second count number indicating a number of oscillations at a second ring oscillator circuit during the sample period is obtained. The second ring oscillator circuit may be associated with (e.g., included in) the sensor and may oscillate at a second oscillation rate (e.g., different than the first oscillation rate). The second oscillation rate may be based only on the first set of physical parameters, which does not include the second physical parameter. The first ring oscillator circuit may include a parameter-based delay circuit associated with the second physical parameter, while the second ring oscillator circuit does not include the parameter-based delay circuit associated with the second physical parameter. In step 1206, a value associated with the second physical parameter at the sensor is determined based on the first count number and the second count number.

Another method is related to daisy chaining, as discussed at, for example, FIGS. 14A and 14B. In some variations, methods described herein may comprise measuring a first value (e.g., pressure value) for a first parameter (e.g., pressure) using a first sensor (e.g., sensor 1402) and transmitting the first value to a second sensor (e.g., sensor 1404) coupled to the first sensor. The method may further comprise measuring a second value (e.g., pressure value, force value, etc.) for a second parameter (e.g., pressure, force, etc.), which may be the same as, or different from, the first parameter, using the second sensor, and producing a serial value that includes the first value and the second value. For example, the serial value may be a concatenation of representations of the first value and the second value. In some variations, the serial value may be a first serial value and the method may further comprise transmitting the first serial value to a third sensor (e.g., sensor 1406) coupled to the second sensor, measuring a third value (e.g., pressure value, force value, light value, etc.) for a third parameter (e.g., pressure, force, light, etc.), which may be the same as, or different than, one or more of the first and second parameters, using the third sensor, and producing a second serial value that includes the first serial value and the third value. In some variations, the method may further comprise transmitting the first and/or second serial values to a compute device configured to determine the first value, the second value, the third value, etc. based on the serial output. In some variations, the first sensor and the second sensor may be operatively coupled to a compute device via only four signals, the four signals being a power signal (e.g., VCC in FIG. 14A), a clock signal (e.g., CLK in FIG. 14A), a ground signal (e.g., GND in FIG. 14A), and an output signal (e.g., SER OUT in FIG. 14A).

Exemplary Sensors

Figure 7A:
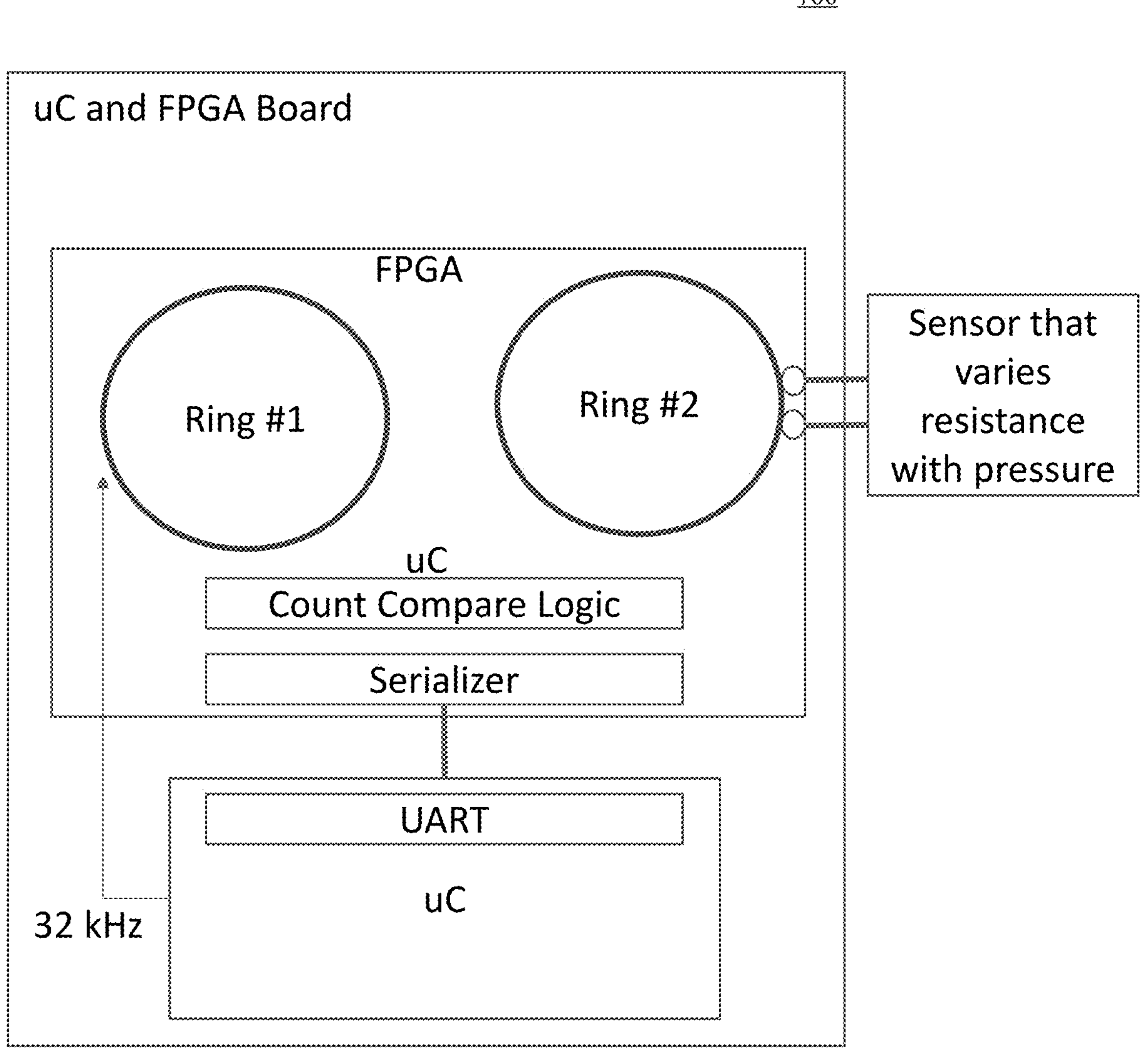
FIGS. 7A, 7B, and 7C are schematic diagrams of exemplary variations of a sensor(s).

FIG. 7A is a schematic diagram of an illustrative variation of a sensor 700 comprising an FPGA circuit and a controller (e.g., microcontroller). The FPGA circuit may comprise a first oscillator ring circuit and a second oscillator ring circuit configured to measure pressure. The first oscillator ring circuit may be disposed entirely on a single substrate (e.g., entirely on a single chip) and may function as the primary offset compensator. The second oscillator ring circuit may comprise a set of pins (e.g., 2 pins) on the FPGA with a first pin coupled to a pressure-sensitive resistor and a second pin input to the same resistor. An input of the FPGA may be coupled to an input clock signal (e.g., 32.768 kHz) output from the microcontroller. A digital output of the FPGA may be coupled to an UART input of the microcontroller.

Figure 7B:
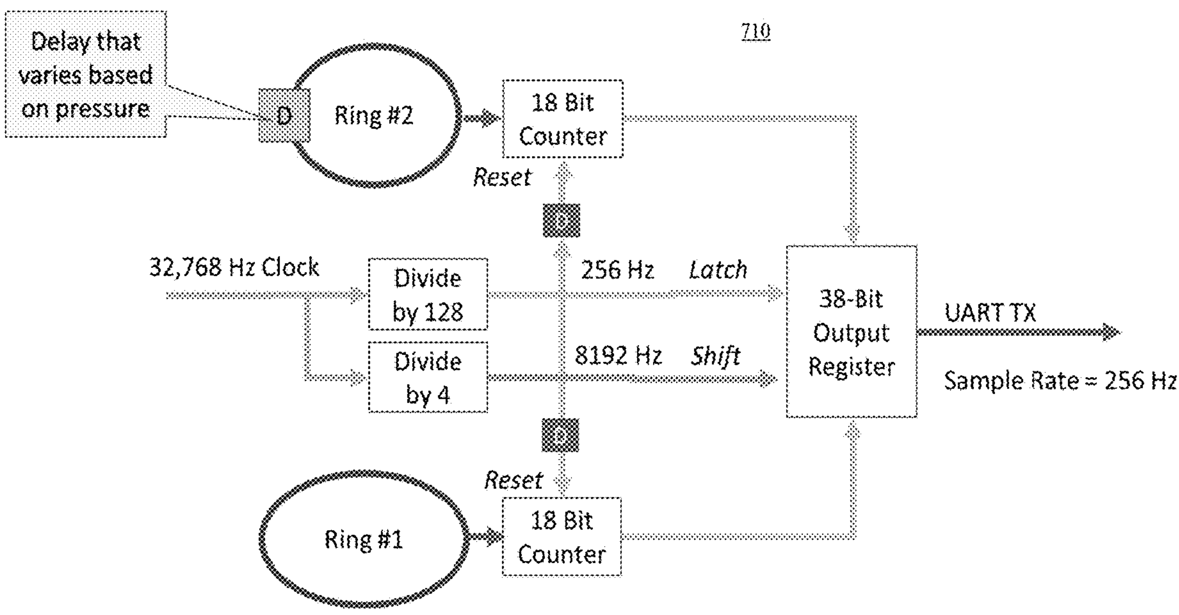

FIG. 7B is an example schematic diagram of circuitry 710 that may be included in an FPGA (e.g., the FPGA from FIG. 7A), a chip, and/or the like. The circuitry includes a first oscillator ring circuit (Ring #1) and a second oscillator ring circuit (Ring #2). The first oscillator ring circuit and the second oscillator ring circuit each oscillate at respective frequencies (e.g., represented by 18 bits, represented by 19 bits, etc.). A difference between the two rings is that Ring #2 will oscillate at a rate that is dependent on the external delay element (while Ring #1 will not oscillate at a rate that is dependent on the external delay element), where the external delay element is configured to have varying delay based on the physical parameter of interest (which is applied pressure in this example). A 32,768 Hz clock is divided (1) in a first clock divider circuit by 128 to generate a 256 Hz signal, and (2) in a second clock divider circuit by 4 to generate an 8,192 Hz signal. The 8,192 Hz signal may be associated with a shift signal at a 38-bit output register, and the 256 Hz signal may be associated with a latch signal at the 38-bit output register. The 256 Hz signal may also be used to reset the 18 bit counters (e.g., at each rising edge or at each falling edge). The 38-bit output register may receive outputs from both 18 bit counters, and generate a signal for sending to a UART.

Figure 7C:
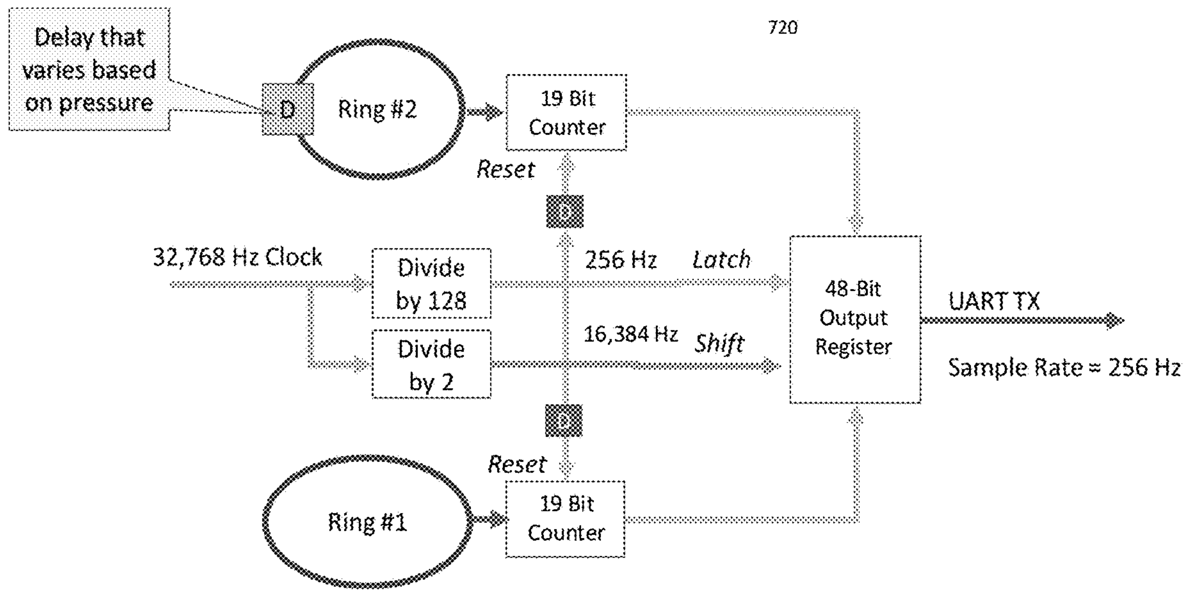

FIG. 7C is an example schematic diagram circuitry 720 that may be included in an FPGA (e.g., the FPGA from FIG. 7A), a chip, and/or the like. The circuitry includes a first oscillator ring circuit (Ring #1) and a second oscillator ring circuit (Ring #2). The first oscillator ring circuit and the second oscillator ring circuit each oscillate at respective frequencies (e.g., represented by 18 bits, represented by 19 bits, etc.). A difference between the two rings is that Ring #2 will oscillate at a rate that is dependent on the external delay element (while Ring #1 will not oscillate at a rate that is dependent on the external delay element), where the external delay element is configured to have varying delay based on the physical parameter of interest (which is applied pressure in this example). A 32,768 Hz clock is divided (1) in a first clock divider circuit by 128 to generate a 256 Hz signal, and (2) in a second clock divider circuit by 2 to generate a 16,384 Hz signal. The 16,384 Hz signal may be associated with a shift signal at a 48-bit output register, and the 256 Hz signal may be associated with a latch signal at the 48-bit output register. In some implementations, the 48-bit output register has 38 bits associated with the two 19 bit counters that may be formed into five bytes (8 bits each byte) plus a start bit and a stop bit for each of the 5 bytes, resulting in the 48 bits. The 256 Hz signal may also be used to reset the 19 bit counters (e.g., at each rising edge or at each falling edge). The 48-bit output register may receive outputs from both 19 bit counters, and generate a signal for sending to a UART.

Exemplary Systems and Devices

The systems and devices described herein are not particularly limited and may be used in a variety of industries and applications. For example, the systems and devices may be used with or otherwise incorporated into medical devices, such as systems and devices for monitoring physiologic states in patients and/or physiologic conditions during medical procedures. In some variations, these systems may include devices comprising an elongate body (e.g., a catheter) with one or more sensors described herein for monitoring physiologic conditions during a medical procedure and/or or monitoring patient physiology over prolonged periods of time during routine and critical medical care. In some instances, these systems may include blood flow control devices. In some variations, the devices may be used to measure (or monitor) blood pressure. In these variations, the devices may be configured to measure blood pressure at any location within the body. For example, the devices may be placed in the central arterial vasculature (e.g., aorta, pulmonary artery) or central venous vasculature (e.g., vena cava), or the peripheral arterial vasculature (e.g., femoral artery, radial artery) or peripheral venous vasculature (e.g. femoral vein, radial vein) and used to measure blood pressure therein. In one variation, the devices may measure blood pressure in the aorta. In other variations, the devices may measure blood pressure in the radial artery. The pressure measurements may or may not be made using devices that include an expandable member, e.g., an expandable balloon.

I. Exemplary Blood Flow Control Devices

Figure 8:
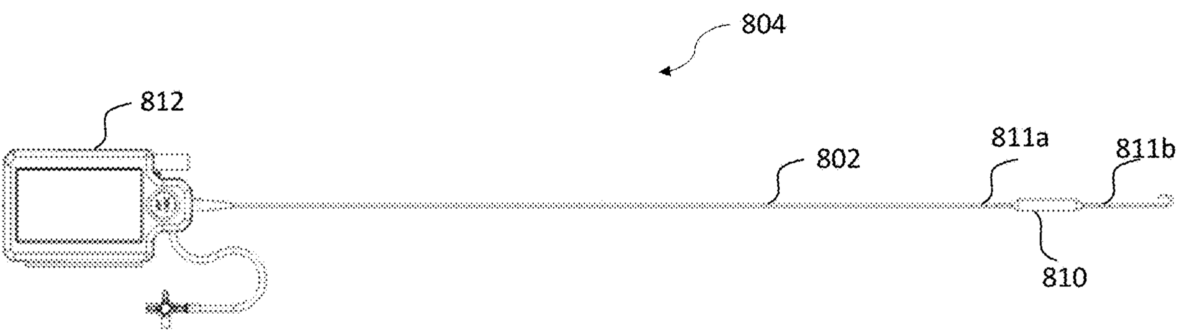
FIG. 8 illustrates an exemplary variation of a blood flow control device including an elongate body with an integrated sensor.

FIG. 8 illustrates an exemplary variation of a blood flow control device 804. The blood flow control device 804 may comprise an elongate body 802, an expandable member 810 (e.g., a balloon) coupled to the elongate body 802 and configured for placement within a blood vessel (e.g., an aorta), and one or more sensors (e.g., 811*a*, 811*b*) coupled to (e.g., integrated with/within) a shaft of the elongate body 802. The one or more sensors may be any of the sensors described herein (e.g., sensor 302, sensor chip 1120) and may be coupled to (e.g., integrated with/within) the shaft of the elongate body in any suitable manner. For example, in some variations, the one or more sensors may be contained within a sensor housing and/or may be coupled to the elongate body via a sleeve. The blood flow control device 804 may be coupled to a controller 812 (e.g., controller 320, microcontroller chip 1130), which may be operably coupled to the one or more sensors and a pump (e.g., a syringe pump). In some variations, the controller 812 may instead be included in a chip with the one or more sensors. The pump may be used to expand and contract (e.g., inflate and deflate) the expandable member. In some variations, the blood flow control device may comprise a plurality of sensors, such as, for example, a first sensor proximal to the expandable member, a second sensor distal to the expandable member, and a third sensor within the expandable member or otherwise configured to measure a parameter within the expandable member. In some variations, each of the plurality of sensors may be configured to measure pressure (e.g., the proximal sensor may measure pressure proximal of the expandable member, the distal sensor may measure pressure distal to the expandable member, and the expandable member sensor may measure pressure within the expandable member).

A. Expandable Member

The expandable member 810 may be one of disposed on, coupled to, integrated with, attached to, and/or affixed to the shaft of the elongate body 802 and a size of the expandable member 810 may be controllable by a controller or a user. For example, the expandable member 810 may be configured to expand and contract and/or inflate and deflate such that the size (e.g., volume) of the expandable member 810 may change during use of the blood flow control device. During use, blood flow may be regulated or otherwise controlled by changing a size of the expandable member 810, thereby altering the area of the blood vessel that is occluded by the expandable member 810. Fluid and/or compressed gas may be delivered through one or more lumens in the elongate body 802 in order to control and/or adjust the size (e.g., volume) of the expandable member 810. Thus, in some variations, the expandable member 810 may be strategically placed within the aorta of a patient and the size of the expandable member 810 may control blood flow through the aorta of the patient such that blood flow distal to expandable member 810 may be impeded to augment blood pressure proximal to expandable member 810. The outer surface of the expandable member 810 may be configured to contact or otherwise interface with the wall(s) of the patient's blood vessel (e.g., at complete occlusion). The expandable member 810 may comprise any suitable elastomeric material (e.g., polyurethane, silicone, etc.). Alternatively, the expandable member may comprise polyester, nylon, etc. In some variations, the expandable member 810 may comprise a shape memory material.

B. Sensor(s)

The blood flow control device may comprise sensors of any variation described herein. For example, in some variations, the blood flow control device may comprise one or more (e.g., two, three, four or more) pressure sensors of any variation described herein integrated into the elongate body 802. In some variations, the pressure sensor(s) may be integrated into the elongate body 802 using a sleeve, as previously described herein. A distal sensor, the position of which is indicated by reference numeral 811*b*, may be disposed between a tip of the elongate body 802 and the expandable member 810. A proximal sensor, the position of which is indicated by reference numeral 811*a*, may be disposed between the base of the elongate body 802 (where the elongate body 802 couples to device controller 812) and the expandable member 810. Each of the distal sensor and the proximal sensor may measure a physiologic condition of the patient, such as physiologic information indicative of blood flow through the aorta, to determine the patient's underlying physiology.

In some variations, the distal sensor 411*b* may be integrated proximal to the expandable 810 member while the proximal sensor 811*a* may be integrated distal to the expandable member 810. For example, the distal sensor 811*b* located on the proximal side of the expandable member 810 may be placed at a distance from the expandable member 810 such that the physiologic data collected from the distal sensor 811*b* may not be disrupted by the blood flow downstream of the expandable member 810. In some variations, the distal sensor 811*b* may be placed at a distance between about 30 mm and about 10 mm, between about 25 mm and about 15 mm, between about 22 mm and about 18 mm from the expandable member 810. For instance, the distal sensor 811*b* may be placed approximately 20 mm from the expandable member 810. In some variations, the proximal sensor 811*a* located on the distal side of the expandable member 810 may be placed between about mm and about 10 mm, between about 25 mm and about 15 mm, or between about 22 mm and about 18 mm from the expandable member. For instance, the proximal sensor 811*a* may be placed approximately 20 mm from the expandable member 810. As discussed above, in some variations, sensors on the elongate body 402 may be situated at a specific distance from the ends of the expandable member 810 so as to acquire the physiologic data upstream and downstream of the expandable member 810.

Note that the terms "proximal" and "distal," as used herein in relation to sensor(s) and/or particular localized blood pressure readings, refer to blood flow directionality from the heart. That is, "proximal" is closer to the heart while "distal" is further from the heart. This is not to be confused with the reversed usage of the terms when described from the perspective of a medical device such as a catheter, where the "distal end" of the medical device would commonly be understood as the end with the expandable element 810 furthest from the device controller 812 and the "proximal end" would be understood as the end closer to the operator.

In some variations, the blood flow control device may further comprise an expandable member sensor (not shown in FIG. 8) integrated into the elongate body 802. For example, the expandable member sensor may be integrated with the expandable member 810 or with the elongate body 802 within the expandable member 810. In variations in which the expandable member sensor is coupled to the elongate body 802, the sensor may be coupled to or integrated with the elongate body 802 using any of sensor integration configurations and/or structures described herein (e.g., sensor housing, sensor sleeve, etc.) In some variations, the expandable member sensor may be coupled to, integrated with and/or disposed on the device controller 812 and may be fluidly coupled to the expandable member. The expandable member sensor may be any one of the sensors described herein and may be configured to detect a characteristic of the expandable member.

C. Controller

The blood flow control device 804 may comprise or may be coupled to one or more controllers. For example, the blood flow control device 804 may comprise a device controller 812, which may be coupled to a base of the elongate body 802. The device controller 812 may be communicatively coupled to one or more sensors, such as, for example, the proximal sensor, the distal sensor, and/or the expandable member sensor. For example, the device controller 812 may be electronically coupled to the proximal sensor, the distal sensor and/or the expandable member sensor.

Figure 21:
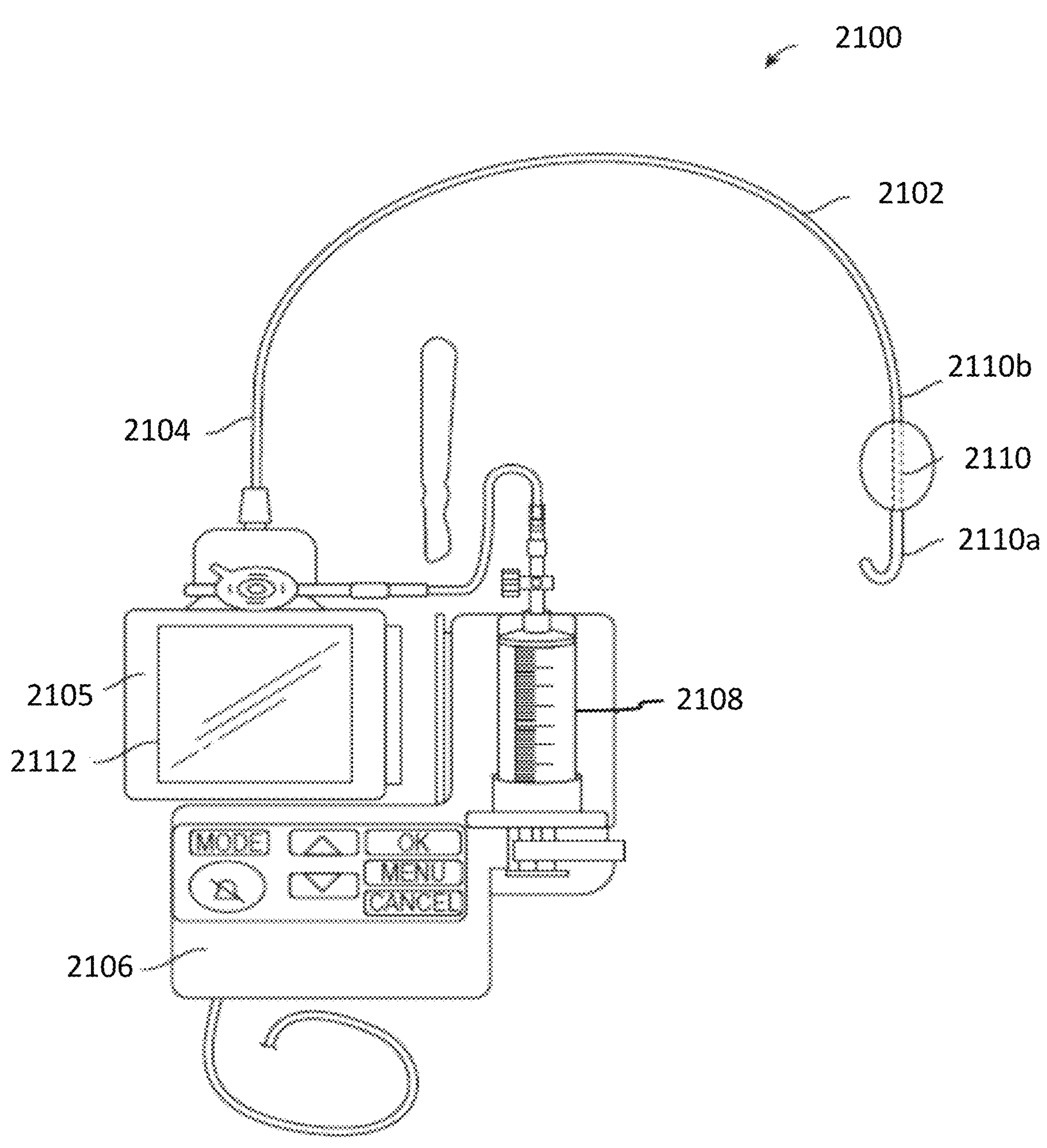
FIG. 21 illustrates an exemplary blood flow control system including a sensor as described herein.

A blood flow control system may comprise a system controller coupled to the blood flow control device (e.g., blood flow control device 804 in FIG. 8). FIG. 21 illustrates an exemplary variation of a blood flow control system 2100. In some variations, the blood flow control system 2100 may comprise a system controller 2106 in addition to the device controller 2112 (e.g., device controller 812 in FIG. 8). The system controller 2106 may be coupled to the blood flow control device 804, for example, via the device controller 2105, or in variations without a device controller 2105, via the elongate body 2102 directly.

In some variations, the device controller 2105 may further comprise a position sensor communicably coupled to a pump 2108 (further described below). In some variations, the position sensor may measure a position of a portion of the pump 2108. For instance, the position sensor may measure a position of a plunger of a syringe pump 2108. The position of the portion of the pump 2108 may be used to infer the amount of fluid that has been delivered to and/or removed from the expandable member 2110.

Additionally or alternatively, the device controller 2105 may comprise a motion sensor (e.g., encoders such as magnetic encoder, optical encoder etc.) communicably coupled to the pump. If the pump 2108 is actuated using a motor, the encoder may monitor the movement of the motor, which may be used to determine the amount of inflation and/or deflation in the expandable member 2110. In some variations, the motion sensor may be a magnetic encoder. Additionally or alternatively, the motion sensor may be an optical encoder. Additionally or alternatively, at least a portion of the system controller 2106 may comprise an optical sensor and/or a contact sensor. The optical sensor and/or contact sensor may be operably coupled to a portion of the pump 2108 to determine a position and/or to track the movement of the pump 2108. The amount of inflation and/or deflation in the expandable member 2110 may be determined based on the position and/or movement of the pump 2108. In some variations, a flow sensor may be employed to determine the amount of inflation and/or deflation in the expandable member 2110.

D. Pump

As depicted in FIG. 21, the blood flow control system 2100 may comprise a pump 2108, which may be operably coupled to the expandable member 2110 to facilitate adjusting a size thereof. The pump 2108 may be contained within (e.g., within an open or closed cavity or chamber) or otherwise carried by or coupled to the housing of the device controller 2105 or the system controller 2106 and may be communicably coupled to one or both of the device controller 2105 and the system controller 2106. The pump 2108 may comprise or otherwise be coupled to an elongate member comprising a lumen (e.g., tubing), which may in turn be coupled to a lumen of the elongate body of the blood flow control device (e.g., an inlet or inflation lumen). In this manner, the pump 2108 may be in fluid communication with the expandable member 2110.

In some variations, the pump may be fluidly coupled to a valve (e.g., a stopcock valve), which may regulate the flow of fluid and/or compressed gas to the expandable member 2110. The size (e.g., volume) of the expandable member may be adjusted using the system and/or device controller 2106, 2105, and the pump 2108.

The sensors described herein may be configured to measure one or more pressures (e.g., blood pressure, expandable member pressure) in order to determine a physiologic condition or state of the patient. The controller(s) (e.g., device controller and/or system controller) communicably coupled to the sensors may be configured to receive data from the sensors that may be indicative of the physiologic condition of the patient and/or the pressure associated with the expandable member. The controller(s) may compare the received data with target data and adjust the volume of the expandable member so as to achieve the target data.

II. Exemplary Pressure Measurement Devices

In some variations, any of the sensors described herein may be incorporated into a device and/or system configured to monitor (e.g., solely monitor, monitor without otherwise controlling blood flow) a physiologic condition or parameter of a patient, such as, for example, blood pressure. The sensors described herein may be placed in various arteries or veins to measure blood pressure, as mentioned above. In other instances, the sensors may measure temperature or another parameter other than blood pressure. The sensors may be placed, e.g., in the aorta, internal jugular artery, pulmonary artery, subclavian artery, femoral artery, radial artery, brachial artery, vena cava, internal jugular vein, or subclavian vein. The sensors may be included on or otherwise positioned within an elongate body (e.g., a catheter) coupled to a controller.

Any of the sensors described herein may be incorporated into a pressure measurement device. In some variations, the pressure measurement device may include a sensor within a sensor housing (as described herein), where the sensor housing is attached to, or otherwise integrated with, an elongate body (e.g., a catheter). The elongate body including the sensor within the sensor housing may be directly introduced into the vasculature to measure pressure (e.g., blood pressure), or configured for advancement through existing arterial or venous lines (e.g., vascular access lines). In some variations, the sensor may be assembled within a tubular housing (e.g., a hypotube or catheter). The sensor and tubular housing may be sized to allow passage of the elongate body into an artery or vein, or through a vascular access line. The sensor may be formed to be physically small in size, e.g., about 0.1 Fr to about 5 Fr (including all values and sub-ranges therein), and may be configured in some instances for integration into a tubular housing having a diameter ranging from about 0.1 Fr to about 10 Fr including all values and sub-ranges therein. For example, the sensor may have a size of about 0.1 Fr, about 0.2 Fr, about 0.3 Fr, about 0.4 Fr, about 0.5 Fr, about Fr, about 0.7 Fr, about 0.8 Fr, about 0.90 Fr, about 1 Fr, about 2 Fr, about 3 Fr, about 4 Fr, or about 5 Fr. The diameter of the tubular housing may be about 0.1 Fr, about 0.2 Fr, about 0.3 Fr, about 0.4 Fr, about 0.5 Fr, about 0.6 Fr, about 0.7 Fr, about 0.8 Fr, about 0.90 Fr, about 1 Fr, about 2 Fr, about 3 Fr, about 4 Fr, about 5 Fr, about 6 Fr, about 7 Fr, about 8 Fr, about 9 Fr, or about 10 Fr. The small size of the sensor may allow space for other components of the pressure measurement device to be included in the elongate body, e.g., stiffening members, fluid lumens, etc. The size and/or diameter of the sensor and the tubular housing will generally be selected based on the diameter of the elongate body, the vascular access line through which it is to be advanced, and/or the bend angle of the artery or vein through which they are to be passed. For example, when the elongate body is about 3 Fr or 4 Fr, the diameter of the sensor and/or the tubular housing may be about 1 Fr. The length of the tubular housing may range from about 5 mm to about 15 mm, including all values and sub-ranges therein. For example, the tubular housing length may be about 5 mm, about 6 mm, about 7 mm, about 8 mm, about 9 mm, about 10 mm, about 11 mm, about 12 mm, about 13 mm, about 14 mm, or about 15 mm.

Figure 20A:
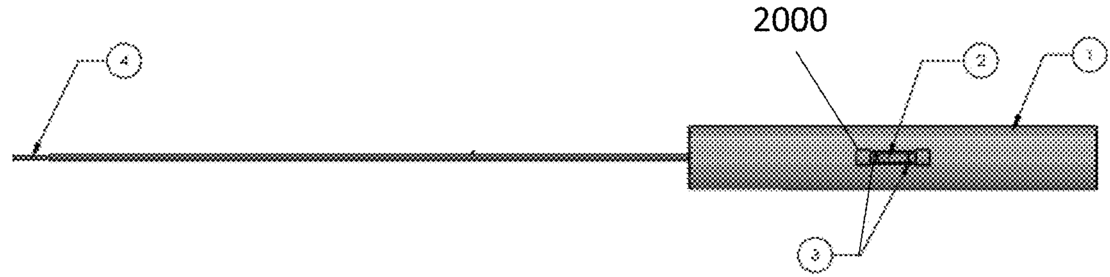
FIGS. 20A and 20B show exemplary views of a sensor housing within an elongate body.
Figure 20B:
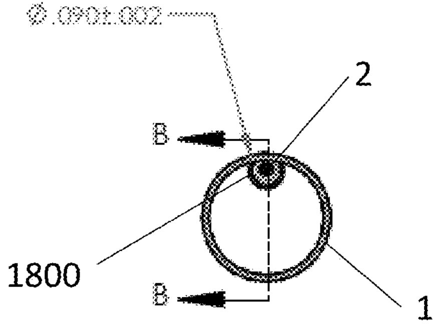

The sensor housing may be attached to the elongate body of the pressure measurement device in various ways. For example, the sensor housing may be attached using one or more structural components (e.g., struts) as previously described. The sensor and structural component(s) may form a sensor assembly. For instance, as shown in FIG. 20A, a sensor housing 2000 may be used to couple the sensor 2 to a elongate body 1. The sensor 2 may be encapsulated in a layer of polymer, e.g., a layer comprising an RTV silicone or a different polymer, in the sensor housing 2000 by, e.g., placing the sensor 2 on the polymer layer and then curing the polymer. Next, the sensor 2 may be encapsulated by covering the sensor 2 with additional polymer, e.g., RTV silicone, and then curing the polymer. The polymer may have a compliance that allows transmission of pressure signals through it so that physiologic conditions, such as, for example, blood pressure, may be transmitted through the polymer to the sensor 2. Separate seals 3 (e.g., RTV silicone seals) may also be disposed within the tubular sensor housing 2000 to protect the sensor 2 from the effects of pressurization. The sensor 2 and sensor housing 2000 collectively (as the sensor assembly) may have a diameter sized to fit within the elongate body 1, and may be designed to have a small diameter (e.g., about 1 Fr). For example, as shown in the cross-sectional view of FIG. 20B, the sensor housing 2000 with the sensor 2 disposed within it may have a size of about 1 Fr, and may be included in an elongate body (e.g., a catheter) 1 with a size of about 7 Fr. A pressure measurement device including a sensor and/or sensor housing of about 1 Fr integrated into a 7 Fr catheter may be useful when the device is to be placed in the aorta to measure blood pressure therein.

The sensors used in the pressure measurement devices may be connected to a printed circuit board assembly (PCBA) housing via one or more wires coupled to the sensor and one or more pins on the PCBA. For example, referring to FIGS. 20A and 22A, the one or more wires (e.g., wire 4 in FIG. 20A) may be disposed within tubing 6 and attached to the PCBA housing 7. The length of the tubing 6 may vary depending on the vascular access site and the target location within the artery or vein at which the parameter (e.g., blood pressure) is to be measured. For example, the length of the tubing may range from about 35 cm to about 70 cm, including all values and sub-ranges therein. For example, the tubing length may be about 35 cm, about 40 cm, about 45 cm, about 50 cm, about 55 cm, about 60 cm, about 65 cm, or about 70 cm.

The PCBA housing may be configured to connect with a controller (e.g., a controller of a blood flow control system) and may include a PCBA network configured to control one or more functions of the sensor. The PCBA housing may comprise a top portion and a bottom portion. The top and bottom portions may be connected via a hinge or an adhesive, or may be attached by snap-fit, friction fit, etc. The adhesive may be tape (e.g., foam tape) on one or more areas on the bottom portion of the housing. Any suitable adhesive may be employed. Referring to FIG. 22B, a double-sided foam tape 9 may be included on two areas of the bottom portion 10 of the housing 7 to adhere the bottom portion 10 to the top portion 11. The top portion 11 of the housing 7 may also include a layer of double-sided foam tape 9 for attaching components of the PCBA network 8 thereto. A coupler (e.g., silicone tubing) 12 may be included in the top portion 11 to connect tubing extending from the sensor (e.g., tubing 6 in FIG. 22A) to the PCBA housing 7 and the wires within the tubing 6 to the PCBA network 8. In some variations, an adhesive may also be used to affix the PCBA housing 7 to the body of a patient. For example, the PCBA housing 7 may be provided on a patch having an adhesive surface configured to adhere the housing to a part of the patient's body, e.g., the skin of the leg, arm, or torso, of a patient.

Although the foregoing variations have, for the purposes of clarity and understanding, been described in some detail by illustration and example, it will be apparent that certain changes and modifications may be practiced, and are intended to fall within the scope of the appended claims. Additionally, it should be understood that the components and characteristics of the systems and devices described herein may be used in any combination. The description of certain elements or characteristics with respect to a specific figure are not intended to be limiting or nor should they be interpreted to suggest that the element cannot be used in combination with any of the other described elements. For all of the variations described herein, the steps of the methods may not be performed sequentially. Some steps are optional such that every step of the methods may not be performed.

I claim:

1. A sensor, comprising:

a first circuit configured to receive an input clock signal and output a first output count signal at a predetermined sample rate;

a second, different circuit configured to receive the input clock signal and output a second output count signal at the predetermined sample rate; and a third circuit coupled to the first circuit and the second circuit, the third circuit configured to generate a third signal based on the first output count signal and the second output count signal.

2. The sensor of claim 1, wherein the first output count signal varies based on a first set of parameters and the second output count signal varies based on a second set of parameters different from the first set of parameters.

3. The sensor of claim 2, wherein the first set of parameters comprise one or more of temperature and voltage.

4. The sensor of claim 2, wherein the second set of parameters comprise temperature, voltage, and one or more of force, pressure, light amplitude, audio amplitude, radiation, and a resistance or capacitance corresponding to a chemical or physical reaction.

5. The sensor of claim 1, wherein the third signal corresponds to one or more of temperature, voltage, force, pressure, light amplitude, and audio amplitude.

6. The sensor of claim 1, wherein a frequency of the predetermined sample rate is less than a frequency of the input clock signal.

7. The sensor of claim 1, wherein the first circuit comprises a first plurality of delay circuits arranged in a ring configuration, and the second circuit comprises a second plurality of delay circuits arranged in another ring configuration.

8. The sensor of claim 7, wherein the first plurality of delay circuits comprises a first plurality of inverter circuits, and the second plurality of delay circuits comprises a second plurality of inverter circuits, the second plurality of delay circuits different from the first plurality of delay circuits.

9. The sensor of claim 8, wherein the first circuit comprises a first counter and a first latch, and the second circuit comprises a second counter and a second latch.

10. The sensor of claim 8, wherein the first plurality of inverter circuits are coupled to a first multiplexer, and the second plurality of inverter circuits are coupled to a second multiplexer.

11. The sensor of claim 8, wherein the first plurality of inverter circuits and the second plurality of inverter circuits are configured in a closed loop with positive feedback.

12. The sensor of claim 7, wherein the first plurality of delay circuits comprises a first resistor-capacitor delay circuit.

13. The sensor of claim 1, wherein the second circuit comprises one or more of a resistor-capacitor delay circuit, a resistor-inductor delay circuit, and a capacitive delay circuit.

14. The sensor of claim 1, wherein the first circuit comprises a first oscillator circuit, and the second circuit comprises a second oscillator circuit.

15. The sensor of claim 1, further comprising a fourth circuit coupled to the third circuit, the fourth circuit configured to receive the input clock signal and output a fourth output count signal at the predetermined sample rate, wherein the third circuit is configured to generate a fifth signal based on a difference between the first output count signal and the fourth output count signal.

16. The sensor of claim 15, wherein the fifth signal corresponds to one or more of temperature, voltage, force, pressure, light amplitude, and audio amplitude.

17. The sensor of claim 1, further comprising a substrate comprising the first circuit, the second circuit, and the third circuit.

18. The sensor of claim 1, further comprising:

a first substrate comprising the first circuit and the second circuit; and a second substrate comprising the third circuit.

19. The sensor of claim 1, further comprising a fourth circuit configured to output the third signal as a digital signal.

20. The sensor of claim 1, further comprising a fourth circuit configured to output the third signal as a set of binary encoded bits at a periodic rate.

21. The sensor of claim 20, wherein the fourth circuit comprises one or more of a wire and an antenna.

22. A device configured to monitor blood pressure, the device comprising:

an elongate body; and the sensor of claim 1 disposed within a tubular sensor housing, wherein the tubular sensor housing is coupled to the elongate body.

23. A method of measuring a parameter, comprising:

receiving an input clock signal;

generating a first output count signal at a predetermined rate based on a first circuit receiving the input clock signal;

generating a second output count signal at the predetermined rate based on a second circuit different from the first circuit receiving the input clock signal; and generating a third signal based on the first output count signal and the second output count signal.

24. The method of claim 23, wherein the third signal represents a sensor value indicative of the parameter.

25. The method of claim 23, wherein the first output count signal varies based on a first set of parameters and the second output count signal varies based on a second set of parameters different from the first set of parameters.

26. The method of claim 25, wherein the first set of parameters comprise temperature and voltage, the second set of parameters comprise temperature, voltage, and pressure, and the parameter is pressure.

27. A sensor for measuring a parameter of an environment surrounding the sensor, comprising:

a first circuit configured to receive an input clock signal and output a first output count signal at a predetermined sample rate;

a second circuit configured to receive the input clock signal and output a second output count signal at the predetermined sample rate; and a third circuit coupled to the first circuit and the second circuit, the third circuit configured to generate a third signal based on the first output count signal and the second output count signal, the third signal representing a sensor value indicative of the parameter.

28. The sensor of claim 27, wherein the first output count signal varies based on a first set of parameters and the second output count signal varies based on a second set of parameters different from the first set of parameters.

29. The sensor of claim 28, wherein the first set of parameters comprise one or more of temperature and voltage, and the second set of parameters comprise temperature, voltage, and one or more of force, pressure, light amplitude, audio amplitude, radiation, and a resistance or capacitance corresponding to a chemical or physical reaction.

30. The sensor of claim 27, wherein the first circuit comprises a first plurality of delay circuits arranged in a ring configuration, and the second circuit comprises a second plurality of delay circuits arranged in another ring configuration.

31. The sensor of claim 30, wherein the first plurality of delay circuits comprises a first plurality of inverter circuits, and the second plurality of delay circuits comprises a second plurality of inverter circuits, the second plurality of delay circuits different from the first plurality of delay circuits.

32. The sensor of claim 31, wherein the first plurality of inverter circuits are coupled to a first multiplexer, and the second plurality of inverter circuits are coupled to a second multiplexer.

33. The sensor of claim 31, wherein the first plurality of inverter circuits and the second plurality of inverter circuits are configured in a closed loop with positive feedback.

34. The sensor of claim 27, wherein the first circuit comprises a first counter and a first latch, and the second circuit comprises a second counter and a second latch.

35. The sensor of claim 27, further comprising:

a fourth circuit coupled to the third circuit, the fourth circuit configured to receive the input clock signal and output a fourth output count signal at the predetermined sample rate, wherein the third circuit is configured to generate a fifth signal based on a difference between the first output count signal and the fourth output count signal.

36. The sensor of claim 27, further comprising:

a first substrate comprising the first circuit and the second circuit; and a second substrate comprising the third circuit.

37. A method of measuring a parameter of an environment surrounding a sensor, comprising:

receiving an input clock signal;

generating a first output count signal at a predetermined rate based on the input clock signal using a first circuit;

generating a second output count signal at the predetermined rate using a second circuit; and generating a third signal based on the first output count signal and the second output count signal, the third signal representing a sensor value indicative of the parameter.

38. The method of claim 37, wherein the parameter corresponds to one or more of temperature, voltage, force, pressure, light amplitude, and audio amplitude.

39. The method of claim 37, wherein the first output count signal varies based on a first set of parameters and the second output count signal varies based on a second set of parameters different from the first set of parameters.

40. The method of claim 39, wherein the first set of parameters comprise temperature and voltage, the second set of parameters comprise temperature, voltage, and pressure, and the parameter is pressure.

41. The method of claim 37, wherein a frequency of the predetermined rate is less than a frequency of the input clock signal.

42. The method of claim 37, further comprising:

outputting the third signal as a set of binary encoded bits at a periodic rate using a fourth circuit.

* * * * *